United States Patent
Peliks et al.

(10) Patent No.: US 10,881,442 B2
(45) Date of Patent: *Jan. 5, 2021

(54) INTEGRITY TESTING METHOD AND APPARATUS FOR DELIVERING VAPOR TO THE UTERUS

(71) Applicant: AEGEA MEDICAL INC., Menlo Park, CA (US)

(72) Inventors: Robert Bilgor Peliks, Redwood City, CA (US); Donnell William Gurskis, Belmont, CA (US); Steven Robert Bacich, Half Moon Bay, CA (US); Uriel Hiram Chee, Santa Cruz, CA (US)

(73) Assignee: AEGEA MEDICAL INC., Menlo Park, CA (US)

( * ) Notice: Subject to any disclaimer, the term of this patent is extended or adjusted under 35 U.S.C. 154(b) by 511 days.

This patent is subject to a terminal disclaimer.

(21) Appl. No.: 15/608,743

(22) Filed: May 30, 2017

(65) Prior Publication Data

US 2017/0258511 A1    Sep. 14, 2017

Related U.S. Application Data

(63) Continuation of application No. 13/648,132, filed on Oct. 9, 2012, now Pat. No. 9,662,060.

(Continued)

(51) Int. Cl.
*A61B 18/04*    (2006.01)
*A61B 5/00*    (2006.01)
(Continued)

(52) U.S. Cl.
CPC .............. *A61B 18/04* (2013.01); *A61B 5/035* (2013.01); *A61B 5/4325* (2013.01);
(Continued)

(58) Field of Classification Search
CPC ..... A61B 5/4325; A61B 18/04; A61B 5/6847; A61B 2018/00577; A61B 2018/048
See application file for complete search history.

(56) References Cited

U.S. PATENT DOCUMENTS 408,899 A    8/1889 Small
697,181 A    4/1902 Smith
(Continued)

FOREIGN PATENT DOCUMENTS

CN    201189204 Y    2/2009
CN    201379631 Y    1/2010
(Continued)

OTHER PUBLICATIONS

Chee et al.; U.S. Appl. No. 16/422,835 entitled "Systems and methods for performing endometrial ablation," filed May 24, 2019.

(Continued)

*Primary Examiner* — Patrick Fernanders
(74) *Attorney, Agent, or Firm* — Shay Glenn LLP

(57) ABSTRACT

A method and system of providing therapy to a patient's uterus is provided, which can include any number of features. The method can include the steps of inserting a uterine device into the uterus and performing a uterine integrity test to determine that the uterus is intact and not perforated. If it is determined that the uterus is not perforated, a patency test can be performed to determine that the uterine device is not clogged or embedded in tissue. If the uterus is intact and the device is not clogged or embedded in tissue, the uterus can be treated with the uterine device, e.g., uterine ablation. Systems for performing these methods are also disclosed.

14 Claims, 10 Drawing Sheets

Related U.S. Application Data

(60) Provisional application No. 61/544,890, filed on Oct. 7, 2011.

(51) Int. Cl.
  *A61B 5/03* (2006.01)
  *A61B 18/00* (2006.01)

(52) U.S. Cl.
  CPC .. *A61B 5/6847* (2013.01); *A61B 2018/00285* (2013.01); *A61B 2018/00559* (2013.01); *A61B 2018/00577* (2013.01); *A61B 2018/048* (2013.01)

(56) References Cited

U.S. PATENT DOCUMENTS

| | | |
|---|---|---|
| 1,719,750 A | 7/1929 | Bridge et al. |
| 3,818,913 A | 6/1974 | Wallach |
| 3,871,374 A | 3/1975 | Bolduc et al. |
| 3,880,168 A | 4/1975 | Berman |
| 3,924,628 A | 12/1975 | Droegemueller et al. |
| 3,930,505 A | 1/1976 | Wallach |
| 4,083,077 A | 4/1978 | Knight et al. |
| 4,447,227 A | 5/1984 | Kotsanis |
| 4,672,962 A | 6/1987 | Hershenson |
| 4,682,596 A | 7/1987 | Bales et al. |
| 4,748,979 A | 6/1988 | Hershenson |
| 4,773,410 A | 9/1988 | Blackmer et al. |
| 4,793,352 A | 12/1988 | Eichenlaub |
| 4,872,920 A | 10/1989 | Flynn et al. |
| 4,898,574 A | 2/1990 | Uchiyama et al. |
| 4,915,113 A | 4/1990 | Holman |
| 4,941,475 A | 7/1990 | Williams et al. |
| 4,950,266 A | 8/1990 | Sinofsky |
| 4,976,711 A | 12/1990 | Parins et al. |
| 4,985,027 A | 1/1991 | Dressel |
| 5,006,119 A | 4/1991 | Acker et al. |
| 5,011,566 A | 4/1991 | Hoffman |
| 5,045,056 A | 9/1991 | Behl |
| 5,078,736 A | 1/1992 | Behl |
| 5,084,043 A | 1/1992 | Hertzmann et al. |
| 5,084,044 A | 1/1992 | Quint |
| 5,102,410 A | 4/1992 | Dressel |
| 5,112,328 A | 5/1992 | Taboada et al. |
| 5,122,138 A | 6/1992 | Manwaring |
| 5,145,935 A | 9/1992 | Hayashi |
| 5,158,536 A | 10/1992 | Sekins et al. |
| 5,162,374 A | 11/1992 | Mulieri et al. |
| 5,190,539 A | 3/1993 | Fletcher et al. |
| 5,217,459 A | 6/1993 | Kamerling |
| 5,217,465 A | 6/1993 | Steppe |
| 5,218,970 A | 6/1993 | Turnbull et al. |
| 5,242,474 A | 9/1993 | Herbst et al. |
| 5,246,436 A | 9/1993 | Rowe |
| 5,263,951 A | 11/1993 | Spears et al. |
| 5,277,201 A | 1/1994 | Stern |
| 5,277,696 A | 1/1994 | Hagen |
| 5,306,274 A | 4/1994 | Long |
| 5,318,014 A | 6/1994 | Carter |
| 5,331,947 A | 7/1994 | Shturman |
| 5,334,190 A | 8/1994 | Seiler |
| 5,344,397 A | 9/1994 | Heaven et al. |
| 5,348,551 A | 9/1994 | Spears et al. |
| 5,352,512 A | 10/1994 | Hoffman |
| 5,411,482 A | 5/1995 | Campbell |
| 5,417,686 A | 5/1995 | Peterson et al. |
| 5,424,620 A | 6/1995 | Cheon et al. |
| 5,433,708 A | 7/1995 | Nichols et al. |
| 5,433,739 A | 7/1995 | Sluijter et al. |
| 5,437,629 A | 8/1995 | Goldrath |
| 5,443,470 A | 8/1995 | Stern et al. |
| 5,445,168 A | 8/1995 | Krebs |
| 5,449,380 A | 9/1995 | Chin |
| 5,451,208 A | 9/1995 | Goldrath |
| 5,462,521 A | 10/1995 | Brucker et al. |
| 5,500,012 A | 3/1996 | Brucker et al. |
| 5,503,638 A | 4/1996 | Cooper et al. |
| 5,505,730 A | 4/1996 | Edwards |
| 5,506,300 A | 4/1996 | Ward et al. |
| 5,524,620 A | 6/1996 | Rosenschein |
| 5,529,076 A | 6/1996 | Schachar |
| 5,540,658 A | 7/1996 | Evans et al. |
| 5,542,928 A | 8/1996 | Evans et al. |
| 5,554,172 A | 9/1996 | Horner et al. |
| 5,562,608 A | 10/1996 | Sekins et al. |
| 5,562,720 A | 10/1996 | Stern et al. |
| 5,584,872 A | 12/1996 | LaFontaine et al. |
| 5,591,157 A | 1/1997 | Hennings et al. |
| 5,616,120 A | 4/1997 | Andrew et al. |
| 5,620,440 A | 4/1997 | Heckele et al. |
| 5,647,871 A | 7/1997 | Levine et al. |
| 5,653,692 A | 8/1997 | Masterson et al. |
| 5,662,671 A | 9/1997 | Barbut et al. |
| 5,665,074 A | 9/1997 | Kelly |
| 5,665,822 A | 9/1997 | Bitler et al. |
| 5,669,907 A | 9/1997 | Platt et al. |
| 5,674,191 A | 10/1997 | Edwards et al. |
| 5,681,282 A | 10/1997 | Eggers et al. |
| 5,683,366 A | 11/1997 | Eggers et al. |
| 5,688,267 A | 11/1997 | Panescu et al. |
| 5,695,507 A | 12/1997 | Auth et al. |
| 5,697,281 A | 12/1997 | Eggers et al. |
| 5,697,536 A | 12/1997 | Eggers et al. |
| 5,697,882 A | 12/1997 | Eggers et al. |
| 5,697,909 A | 12/1997 | Eggers et al. |
| 5,700,262 A | 12/1997 | Acosta et al. |
| 5,707,352 A | 1/1998 | Sekins et al. |
| 5,730,719 A | 3/1998 | Edwards |
| 5,735,811 A | 4/1998 | Brisken |
| 5,741,247 A | 4/1998 | Rizoiu et al. |
| 5,741,248 A | 4/1998 | Stern et al. |
| 5,743,870 A | 4/1998 | Edwards |
| 5,752,965 A | 5/1998 | Francis et al. |
| 5,754,717 A | 5/1998 | Esch |
| 5,755,753 A | 5/1998 | Knowlton |
| 5,769,880 A | 6/1998 | Truckai et al. |
| 5,782,914 A | 7/1998 | Schankereli |
| 5,785,521 A | 7/1998 | Rizoiu et al. |
| 5,800,379 A | 9/1998 | Edwards |
| 5,800,482 A | 9/1998 | Pomeranz et al. |
| 5,800,493 A | 9/1998 | Stevens et al. |
| 5,810,764 A | 9/1998 | Eggers et al. |
| 5,820,580 A | 10/1998 | Edwards et al. |
| 5,824,703 A | 10/1998 | Clark |
| 5,827,268 A | 10/1998 | Laufer |
| 5,836,896 A | 11/1998 | Rosenschein |
| 5,836,906 A | 11/1998 | Edwards |
| 5,843,019 A | 12/1998 | Eggers et al. |
| 5,871,469 A | 2/1999 | Eggers et al. |
| 5,873,855 A | 2/1999 | Eggers et al. |
| 5,879,329 A | 3/1999 | Ginsburg |
| 5,885,243 A | 3/1999 | Capetan et al. |
| 5,888,198 A | 3/1999 | Eggers et al. |
| 5,891,094 A | 4/1999 | Masterson et al. |
| 5,891,095 A | 4/1999 | Eggers et al. |
| 5,891,134 A | 4/1999 | Goble et al. |
| 5,891,457 A | 4/1999 | Neuwirth |
| 5,902,272 A | 5/1999 | Eggers et al. |
| 5,911,734 A | 6/1999 | Tsugita et al. |
| 5,913,856 A | 6/1999 | Chia et al. |
| 5,938,660 A | 8/1999 | Swartz et al. |
| 5,944,686 A | 8/1999 | Patterson et al. |
| 5,944,715 A | 8/1999 | Goble et al. |
| 5,957,919 A | 9/1999 | Laufer |
| 5,964,752 A | 10/1999 | Stone |
| 5,968,037 A | 10/1999 | Rizoiu et al. |
| 5,980,504 A | 11/1999 | Sharkey et al. |
| 5,986,662 A | 11/1999 | Argiro et al. |
| 5,989,212 A | 11/1999 | Sussman et al. |
| 5,989,249 A | 11/1999 | Kirwan |
| 5,989,445 A | 11/1999 | Wise et al. |
| 5,997,499 A | 12/1999 | Sussman et al. |
| 6,004,509 A | 12/1999 | Dey et al. |
| 6,015,406 A | 1/2000 | Goble et al. |

(56) References Cited

U.S. PATENT DOCUMENTS

| | | |
|---|---|---|
| 6,024,095 A | 2/2000 | Stanley |
| 6,024,733 A | 2/2000 | Eggers et al. |
| 6,027,501 A | 2/2000 | Goble et al. |
| 6,032,077 A | 2/2000 | Pomeranz |
| 6,045,532 A | 4/2000 | Eggers et al. |
| 6,045,549 A | 4/2000 | Smethers et al. |
| 6,047,700 A | 4/2000 | Eggers et al. |
| 6,053,172 A | 4/2000 | Hovda et al. |
| 6,053,909 A | 4/2000 | Shadduck |
| 6,056,746 A | 5/2000 | Goble et al. |
| 6,057,689 A | 5/2000 | Saadat |
| 6,059,011 A | 5/2000 | Giolo |
| 6,063,079 A | 5/2000 | Hovda et al. |
| 6,063,081 A | 5/2000 | Mulier et al. |
| 6,066,134 A | 5/2000 | Eggers et al. |
| 6,066,139 A | 5/2000 | Ryan et al. |
| 6,080,128 A | 6/2000 | Sussman et al. |
| 6,080,151 A | 6/2000 | Swartz et al. |
| 6,083,255 A | 7/2000 | Laufer et al. |
| 6,086,585 A | 7/2000 | Hovda et al. |
| 6,095,149 A | 8/2000 | Sharkey et al. |
| 6,099,251 A | 8/2000 | LaFleur |
| 6,102,046 A | 8/2000 | Weinstein et al. |
| 6,102,885 A | 8/2000 | Bass |
| 6,105,581 A | 8/2000 | Eggers et al. |
| 6,106,516 A | 8/2000 | Massengill |
| 6,109,268 A | 8/2000 | Thapliyal et al. |
| 6,113,597 A | 9/2000 | Eggers et al. |
| 6,113,722 A | 9/2000 | Hoffman et al. |
| 6,117,109 A | 9/2000 | Eggers et al. |
| 6,126,682 A | 10/2000 | Sharkey et al. |
| 6,130,671 A | 10/2000 | Argiro |
| 6,139,571 A | 10/2000 | Fuller et al. |
| 6,149,620 A | 11/2000 | Baker et al. |
| 6,156,036 A | 12/2000 | Sussman et al. |
| 6,159,160 A | 12/2000 | Hsei et al. |
| 6,159,194 A | 12/2000 | Eggers et al. |
| 6,159,207 A | 12/2000 | Yoon |
| 6,159,208 A | 12/2000 | Hovda et al. |
| 6,162,210 A | 12/2000 | Shadduck |
| 6,162,232 A | 12/2000 | Shadduck |
| 6,174,308 B1 | 1/2001 | Goble et al. |
| 6,179,805 B1 | 1/2001 | Sussman et al. |
| 6,179,824 B1 | 1/2001 | Eggers et al. |
| 6,179,836 B1 | 1/2001 | Eggers et al. |
| 6,183,469 B1 | 2/2001 | Thapliyal et al. |
| 6,190,381 B1 | 2/2001 | Olsen et al. |
| 6,194,066 B1 | 2/2001 | Hoffman |
| 6,196,989 B1 | 3/2001 | Padget et al. |
| 6,200,333 B1 | 3/2001 | Laufer |
| 6,203,542 B1 | 3/2001 | Ellsberry et al. |
| 6,210,402 B1 | 4/2001 | Olsen et al. |
| 6,210,404 B1 | 4/2001 | Shadduck |
| 6,210,405 B1 | 4/2001 | Goble et al. |
| 6,219,059 B1 | 4/2001 | Argiro |
| 6,224,592 B1 | 5/2001 | Eggers et al. |
| 6,228,078 B1 | 5/2001 | Eggers et al. |
| 6,228,081 B1 | 5/2001 | Goble |
| 6,228,082 B1 | 5/2001 | Baker et al. |
| 6,231,567 B1 | 5/2001 | Rizoiu et al. |
| 6,235,020 B1 | 5/2001 | Cheng et al. |
| 6,238,391 B1 | 5/2001 | Olsen et al. |
| 6,254,597 B1 | 7/2001 | Rizoiu et al. |
| 6,254,600 B1 | 7/2001 | Willink et al. |
| 6,261,286 B1 | 7/2001 | Goble et al. |
| 6,261,311 B1 | 7/2001 | Sharkey et al. |
| 6,264,650 B1 | 7/2001 | Hovda et al. |
| 6,264,651 B1 | 7/2001 | Underwood et al. |
| 6,264,652 B1 | 7/2001 | Eggers et al. |
| 6,277,112 B1 | 8/2001 | Underwood et al. |
| 6,277,114 B1 | 8/2001 | Bullivant et al. |
| 6,283,910 B1 | 9/2001 | Bradshaw et al. |
| 6,283,961 B1 | 9/2001 | Underwood et al. |
| 6,283,989 B1 | 9/2001 | Laufer et al. |
| 6,290,715 B1 | 9/2001 | Sharkey et al. |
| 6,293,942 B1 | 9/2001 | Goble et al. |
| 6,296,636 B1 | 10/2001 | Cheng et al. |
| 6,296,638 B1 | 10/2001 | Davison et al. |
| 6,299,633 B1 | 10/2001 | Laufer |
| 6,300,150 B1 | 10/2001 | Venkatasubramanian |
| 6,306,129 B1 | 10/2001 | Little et al. |
| 6,306,134 B1 | 10/2001 | Goble et al. |
| 6,309,387 B1 | 10/2001 | Eggers et al. |
| 6,312,408 B1 | 11/2001 | Eggers et al. |
| 6,312,474 B1 | 11/2001 | Francis et al. |
| 6,315,755 B1 | 11/2001 | Sussman |
| 6,319,221 B1 | 11/2001 | Savage et al. |
| 6,322,549 B1 | 11/2001 | Eggers et al. |
| 6,327,505 B1 | 12/2001 | Medhkour et al. |
| 6,328,735 B1 | 12/2001 | Curley et al. |
| 6,331,171 B1 | 12/2001 | Cohen |
| 6,355,032 B1 | 3/2002 | Hovda et al. |
| 6,361,531 B1 | 3/2002 | Hissong |
| 6,363,937 B1 | 4/2002 | Hovda et al. |
| 6,364,877 B1 | 4/2002 | Goble et al. |
| 6,375,635 B1 | 4/2002 | Moutafis et al. |
| 6,379,350 B1 | 4/2002 | Sharkey et al. |
| 6,379,351 B1 | 4/2002 | Thapliyal et al. |
| 6,387,088 B1 | 5/2002 | Shattuck et al. |
| 6,388,043 B1 | 5/2002 | Langer et al. |
| 6,391,025 B1 | 5/2002 | Weinstein et al. |
| 6,394,949 B1 | 5/2002 | Crowley et al. |
| 6,394,996 B1 | 5/2002 | Lawrence et al. |
| 6,398,759 B1 | 6/2002 | Sussman et al. |
| 6,398,775 B1 | 6/2002 | Perkins et al. |
| 6,409,699 B1 | 6/2002 | Ash |
| 6,409,723 B1 | 6/2002 | Edwards |
| 6,416,507 B1 | 7/2002 | Eggers et al. |
| 6,416,508 B1 | 7/2002 | Eggers et al. |
| 6,416,509 B1 | 7/2002 | Goble et al. |
| 6,432,103 B1 | 8/2002 | Ellsberry et al. |
| 6,440,089 B1 | 8/2002 | Shine |
| 6,443,947 B1 | 9/2002 | Marko et al. |
| 6,458,231 B1 | 10/2002 | Wapner et al. |
| 6,461,350 B1 | 10/2002 | Underwood et al. |
| 6,461,354 B1 | 10/2002 | Olsen et al. |
| 6,464,694 B1 | 10/2002 | Massengill |
| 6,464,695 B2 | 10/2002 | Hovda et al. |
| 6,468,270 B1 | 10/2002 | Hovda et al. |
| 6,468,274 B1 | 10/2002 | Alleyne et al. |
| 6,468,313 B1 | 10/2002 | Claeson et al. |
| 6,475,215 B1 | 11/2002 | Tanrisever |
| 6,482,201 B1 | 11/2002 | Olsen et al. |
| 6,488,673 B1 | 12/2002 | Laufer et al. |
| 6,493,589 B1 | 12/2002 | Medhkour et al. |
| 6,500,173 B2 | 12/2002 | Underwood et al. |
| 6,508,816 B2 | 1/2003 | Shadduck |
| 6,510,854 B2 | 1/2003 | Goble |
| 6,517,533 B1 | 2/2003 | Swaminathan |
| 6,522,930 B1 | 2/2003 | Schaer et al. |
| 6,527,761 B1 | 3/2003 | Soltesz et al. |
| 6,527,766 B1 | 3/2003 | Bair |
| 6,540,741 B1 | 4/2003 | Underwood et al. |
| 6,544,211 B1 | 4/2003 | Andrew et al. |
| 6,544,261 B2 | 4/2003 | Ellsberry et al. |
| 6,547,784 B1 | 4/2003 | Thompson et al. |
| 6,551,271 B2 | 4/2003 | Nguyen |
| 6,551,274 B2 | 4/2003 | Heiner |
| 6,554,780 B1 | 4/2003 | Sampson et al. |
| 6,557,559 B1 | 5/2003 | Eggers et al. |
| 6,558,379 B1 | 5/2003 | Batchelor et al. |
| 6,565,561 B1 | 5/2003 | Goble et al. |
| 6,569,146 B1 | 5/2003 | Werner et al. |
| 6,575,929 B2 | 6/2003 | Sussman et al. |
| 6,575,933 B1 | 6/2003 | Wittenberger et al. |
| 6,575,968 B1 | 6/2003 | Eggers et al. |
| 6,579,270 B2 | 6/2003 | Sussman et al. |
| 6,582,423 B1 | 6/2003 | Thapliyal et al. |
| 6,585,639 B1 | 7/2003 | Kotmel et al. |
| 6,588,613 B1 | 7/2003 | Pechenik et al. |
| 6,589,201 B1 | 7/2003 | Sussman et al. |
| 6,589,237 B2 | 7/2003 | Woloszko et al. |
| 6,592,594 B2 | 7/2003 | Rimbaugh et al. |
| 6,595,990 B1 | 7/2003 | Weinstein et al. |

(56) References Cited

U.S. PATENT DOCUMENTS

| | | |
|---|---|---|
| 6,599,311 B1 | 7/2003 | Biggs et al. |
| 6,602,248 B1 | 8/2003 | Sharps et al. |
| 6,610,043 B1 | 8/2003 | Ingenito |
| 6,620,155 B2 | 9/2003 | Underwood et al. |
| 6,623,444 B2 | 9/2003 | Babaev |
| 6,626,855 B1 | 9/2003 | Weng et al. |
| 6,629,974 B2 | 10/2003 | Penny et al. |
| 6,632,193 B1 | 10/2003 | Davison et al. |
| 6,632,220 B1 | 10/2003 | Eggers et al. |
| 6,634,363 B1 | 10/2003 | Danek et al. |
| 6,653,525 B2 | 11/2003 | Ingenito et al. |
| 6,669,685 B1 | 12/2003 | Rizoiu et al. |
| 6,669,694 B2 | 12/2003 | Shadduck |
| 6,676,628 B2 | 1/2004 | Sussman et al. |
| 6,676,629 B2 | 1/2004 | Andrew et al. |
| 6,679,264 B1 | 1/2004 | Deem et al. |
| 6,679,879 B2 | 1/2004 | Shadduck |
| 6,692,494 B1 | 2/2004 | Cooper et al. |
| 6,695,839 B2 | 2/2004 | Sharkey et al. |
| 6,699,212 B1 | 3/2004 | Kadziauskas et al. |
| 6,699,244 B2 | 3/2004 | Carranza et al. |
| 6,708,056 B2 | 3/2004 | Duchon et al. |
| 6,712,811 B2 | 3/2004 | Underwood et al. |
| 6,712,812 B2 | 3/2004 | Roschak et al. |
| 6,719,754 B2 | 4/2004 | Underwood et al. |
| 6,726,684 B1 | 4/2004 | Woloszko et al. |
| 6,726,708 B2 | 4/2004 | Lasheras |
| 6,746,447 B2 | 6/2004 | Davison et al. |
| 6,749,604 B1 | 6/2004 | Eggers et al. |
| 6,755,794 B2 | 6/2004 | Soukup |
| 6,758,846 B2 | 7/2004 | Goble et al. |
| 6,763,836 B2 | 7/2004 | Tasto et al. |
| 6,766,202 B2 | 7/2004 | Underwood et al. |
| 6,770,070 B1 | 8/2004 | Balbierz |
| 6,770,071 B2 | 8/2004 | Woloszko et al. |
| 6,772,012 B2 | 8/2004 | Ricart et al. |
| 6,773,431 B2 | 8/2004 | Eggers et al. |
| 6,776,765 B2 | 8/2004 | Soukup et al. |
| 6,780,180 B1 | 8/2004 | Goble et al. |
| 6,805,130 B2 | 10/2004 | Tasto et al. |
| 6,813,520 B2 | 11/2004 | Truckai et al. |
| 6,832,996 B2 | 12/2004 | Woloszko et al. |
| 6,837,884 B2 | 1/2005 | Woloszko |
| 6,837,887 B2 | 1/2005 | Woloszko et al. |
| 6,837,888 B2 | 1/2005 | Ciarrocca et al. |
| 6,852,108 B2 | 2/2005 | Barry et al. |
| 6,860,847 B2 | 3/2005 | Alferness et al. |
| 6,875,194 B2 | 4/2005 | MacKool |
| 6,896,672 B1 | 5/2005 | Eggers et al. |
| 6,896,674 B1 | 5/2005 | Woloszko et al. |
| 6,896,675 B2 | 5/2005 | Leung et al. |
| 6,896,690 B1 | 5/2005 | Lambrecht et al. |
| 6,901,927 B2 | 6/2005 | Deem et al. |
| 6,904,909 B2 | 6/2005 | Andreas et al. |
| 6,907,881 B2 | 6/2005 | Suki et al. |
| 6,911,028 B2 | 6/2005 | Shadduck |
| 6,915,806 B2 | 7/2005 | Pacek et al. |
| 6,918,903 B2 | 7/2005 | Bass |
| 6,921,385 B2 | 7/2005 | Clements et al. |
| 6,929,640 B1 | 8/2005 | Underwood et al. |
| 6,929,642 B2 | 8/2005 | Xiao et al. |
| 6,949,096 B2 | 9/2005 | Davison et al. |
| 6,955,675 B2 | 10/2005 | Jain |
| 6,960,204 B2 | 11/2005 | Eggers et al. |
| 6,962,584 B1 | 11/2005 | Stone et al. |
| 6,972,014 B2 | 12/2005 | Eum et al. |
| 6,978,174 B2 | 12/2005 | Gelfand et al. |
| 6,986,769 B2 | 1/2006 | Nelson et al. |
| 6,991,028 B2 | 1/2006 | Comeaux et al. |
| 6,991,631 B2 | 1/2006 | Woloszko et al. |
| 7,004,940 B2 | 2/2006 | Ryan et al. |
| 7,004,941 B2 | 2/2006 | Tvinnereim et al. |
| 7,022,088 B2 | 4/2006 | Keast et al. |
| 7,031,504 B1 | 4/2006 | Argiro et al. |
| 7,070,596 B1 | 7/2006 | Woloszko et al. |
| 7,083,612 B2 | 8/2006 | Littrup et al. |
| 7,094,215 B2 | 8/2006 | Davison et al. |
| 7,094,249 B1 | 8/2006 | Broome et al. |
| 7,101,367 B2 | 9/2006 | Xiao et al. |
| 7,104,986 B2 | 9/2006 | Hovda et al. |
| 7,105,007 B2 | 9/2006 | Hibler |
| RE39,358 E | 10/2006 | Goble |
| 7,128,748 B2 | 10/2006 | Mooradian et al. |
| 7,131,969 B1 | 11/2006 | Hovda et al. |
| 7,136,064 B2 | 11/2006 | Zuiderveld |
| 7,144,402 B2 | 12/2006 | Kuester |
| 7,144,588 B2 | 12/2006 | Oray et al. |
| 7,162,303 B2 | 1/2007 | Levin et al. |
| 7,169,143 B2 | 1/2007 | Eggers et al. |
| 7,179,255 B2 | 2/2007 | Lettice et al. |
| 7,186,234 B2 | 3/2007 | Dahla et al. |
| 7,192,400 B2 | 3/2007 | Campbell et al. |
| 7,192,428 B2 | 3/2007 | Eggers et al. |
| 7,201,750 B1 | 4/2007 | Eggers et al. |
| 7,217,268 B2 | 5/2007 | Eggers et al. |
| 7,233,820 B2 | 6/2007 | Gilboa |
| 7,235,070 B2 | 6/2007 | Vanney |
| 7,241,293 B2 | 7/2007 | Davison |
| 7,270,658 B2 | 9/2007 | Woloszko et al. |
| 7,270,659 B2 | 9/2007 | Ricart et al. |
| 7,270,661 B2 | 9/2007 | Dahla et al. |
| 7,276,063 B2 | 10/2007 | Davison et al. |
| 7,297,143 B2 | 11/2007 | Woloszko et al. |
| 7,297,145 B2 | 11/2007 | Woloszko et al. |
| 7,311,708 B2 | 12/2007 | McClurken |
| 7,320,325 B2 | 1/2008 | Duchon et al. |
| 7,335,195 B2 | 2/2008 | Mehier |
| 7,347,859 B2 | 3/2008 | Garabedian et al. |
| 7,524,315 B2 | 4/2009 | Blott et al. |
| 7,585,295 B2 | 9/2009 | Ben-Nun |
| 7,617,005 B2 | 11/2009 | Demarais et al. |
| 7,620,451 B2 | 11/2009 | Demarais et al. |
| 7,653,438 B2 | 1/2010 | Deem et al. |
| 7,756,583 B2 | 7/2010 | Demarais et al. |
| 7,815,616 B2 | 10/2010 | Boehringer et al. |
| 7,815,646 B2 | 10/2010 | Hart |
| 7,853,333 B2 | 12/2010 | Demarais |
| 7,873,417 B2 | 1/2011 | Demarais et al. |
| 7,937,143 B2 | 5/2011 | Demarais et al. |
| 7,993,323 B2 | 8/2011 | Barry et al. |
| 8,131,371 B2 | 3/2012 | Demarais et al. |
| 8,145,316 B2 | 3/2012 | Deem et al. |
| 8,145,317 B2 | 3/2012 | Demarais et al. |
| 8,150,519 B2 | 4/2012 | Demarais et al. |
| 8,150,520 B2 | 4/2012 | Demarais et al. |
| 8,175,711 B2 | 5/2012 | Demarais et al. |
| 8,192,424 B2 | 6/2012 | Woloszko |
| 8,197,470 B2 | 6/2012 | Sharkey et al. |
| 8,216,217 B2 | 7/2012 | Sharkey et al. |
| 8,221,401 B2 | 7/2012 | Sharkey et al. |
| 8,221,403 B2 | 7/2012 | Sharkey et al. |
| 8,313,485 B2 | 11/2012 | Shadduck |
| 8,574,226 B2 | 11/2013 | Shadduck |
| 8,579,888 B2 | 11/2013 | Hoey et al. |
| 8,579,892 B2 | 11/2013 | Hoey et al. |
| 8,585,645 B2 | 11/2013 | Barry et al. |
| 8,585,692 B2 | 11/2013 | Shadduck et al. |
| 8,758,341 B2 | 6/2014 | Shadduck |
| 8,801,702 B2 | 8/2014 | Hoey et al. |
| 8,900,223 B2 | 12/2014 | Shadduck |
| 9,113,944 B2 | 8/2015 | Shadduck |
| 9,433,457 B2 | 9/2016 | Shadduck |
| 9,615,875 B2 | 4/2017 | Shadduck |
| 9,662,060 B2 | 5/2017 | Peliks et al. |
| 9,907,599 B2 | 3/2018 | Hoey et al. |
| 10,524,847 B2 | 1/2020 | Shadduck |
| 10,548,653 B2 | 2/2020 | Hoey et al. |
| 2002/0007180 A1 | 1/2002 | Wittenberger et al. |
| 2002/0013601 A1 | 1/2002 | Nobles et al. |
| 2002/0019627 A1 | 2/2002 | Maguire et al. |
| 2002/0077516 A1 | 6/2002 | Flanigan |
| 2002/0078956 A1 | 6/2002 | Sharpe et al. |
| 2002/0111386 A1 | 8/2002 | Sekins et al. |
| 2002/0128638 A1 | 9/2002 | Chauvet et al. |

(56) References Cited

U.S. PATENT DOCUMENTS

| | | |
|---|---|---|
| 2002/0133147 A1 | 9/2002 | Marchitto et al. |
| 2002/0151917 A1 | 10/2002 | Barry |
| 2002/0161326 A1 | 10/2002 | Sussman et al. |
| 2002/0173815 A1 | 11/2002 | Hogendijk et al. |
| 2002/0177846 A1 | 11/2002 | Muller et al. |
| 2003/0028189 A1 | 2/2003 | Woloszko et al. |
| 2003/0097126 A1 | 5/2003 | Woloszko et al. |
| 2003/0099279 A1 | 5/2003 | Venkatasubramanian et al. |
| 2003/0130738 A1 | 7/2003 | Hovda et al. |
| 2003/0144654 A1 | 7/2003 | Hilal |
| 2003/0158545 A1 | 8/2003 | Hovda et al. |
| 2003/0163178 A1 | 8/2003 | Davison et al. |
| 2003/0181922 A1 | 9/2003 | Alferness |
| 2003/0212394 A1 | 11/2003 | Pearson et al. |
| 2003/0217962 A1 | 11/2003 | Childers et al. |
| 2003/0220604 A1 | 11/2003 | Al-Anazi |
| 2003/0225364 A1 | 12/2003 | Kraft et al. |
| 2004/0002698 A1 | 1/2004 | Hua Xiao et al. |
| 2004/0024399 A1 | 2/2004 | Sharps et al. |
| 2004/0047855 A1 | 3/2004 | Ingenito |
| 2004/0049180 A1 | 3/2004 | Sharps et al. |
| 2004/0055606 A1 | 3/2004 | Hendricksen et al. |
| 2004/0068306 A1 | 4/2004 | Shadduck |
| 2004/0116922 A1 | 6/2004 | Hovda et al. |
| 2004/0199226 A1 | 10/2004 | Shadduck |
| 2004/0230190 A1 | 11/2004 | Dahla et al. |
| 2005/0010205 A1 | 1/2005 | Hovda et al. |
| 2005/0119650 A1 | 6/2005 | Sanders et al. |
| 2005/0143728 A1 | 6/2005 | Sampson et al. |
| 2005/0166925 A1 | 8/2005 | Wilson et al. |
| 2005/0171574 A1 | 8/2005 | Rubinsky et al. |
| 2005/0171582 A1 | 8/2005 | Matlock |
| 2005/0177147 A1 | 8/2005 | Vancelette et al. |
| 2005/0215991 A1 | 9/2005 | Altman et al. |
| 2005/0222485 A1 | 10/2005 | Shaw et al. |
| 2005/0228423 A1 | 10/2005 | Khashayar et al. |
| 2005/0228424 A1 | 10/2005 | Khashayar et al. |
| 2005/0240171 A1 | 10/2005 | Forrest |
| 2005/0240239 A1 | 10/2005 | Boveja et al. |
| 2005/0267467 A1 | 12/2005 | Paul et al. |
| 2005/0283143 A1 | 12/2005 | Rizoiu |
| 2006/0004400 A1 | 1/2006 | McGurk et al. |
| 2006/0047291 A1 | 3/2006 | Barry |
| 2006/0058831 A1 | 3/2006 | Atad |
| 2006/0085054 A1 | 4/2006 | Zikorus et al. |
| 2006/0100619 A1 | 5/2006 | McClurken et al. |
| 2006/0130830 A1 | 6/2006 | Barry |
| 2006/0135955 A1 | 6/2006 | Shadduck |
| 2006/0142783 A1 | 6/2006 | Lewis et al. |
| 2006/0161147 A1 | 7/2006 | Privitera et al. |
| 2006/0161233 A1 | 7/2006 | Barry et al. |
| 2006/0200076 A1 | 9/2006 | Gonzalez et al. |
| 2006/0206150 A1 | 9/2006 | Demarais et al. |
| 2006/0224154 A1 | 10/2006 | Shadduck et al. |
| 2006/0265053 A1 | 11/2006 | Hunt |
| 2006/0271111 A1 | 11/2006 | Demarais et al. |
| 2007/0021713 A1 | 1/2007 | Kumar et al. |
| 2007/0032785 A1 | 2/2007 | Diederich et al. |
| 2007/0066990 A1 | 3/2007 | Marsella et al. |
| 2007/0129720 A1 | 6/2007 | Demarais et al. |
| 2007/0129760 A1 | 6/2007 | Demarais et al. |
| 2007/0129761 A1 | 6/2007 | Demarais et al. |
| 2007/0135875 A1 | 6/2007 | Demarais et al. |
| 2007/0225744 A1 | 9/2007 | Nobles et al. |
| 2007/0239197 A1 | 10/2007 | Dubey et al. |
| 2007/0288051 A1 | 12/2007 | Beyer et al. |
| 2008/0033493 A1 | 2/2008 | Deckman et al. |
| 2008/0077201 A1 | 3/2008 | Levinson et al. |
| 2008/0125747 A1 | 5/2008 | Prokop |
| 2008/0132826 A1 | 6/2008 | Shadduck et al. |
| 2008/0135053 A1 | 6/2008 | Gruber et al. |
| 2008/0161788 A1 | 7/2008 | Dando et al. |
| 2008/0167664 A1 | 7/2008 | Payne et al. |
| 2008/0249467 A1 | 10/2008 | Burnett et al. |
| 2009/0024108 A1 | 1/2009 | Lee-Sepsick et al. |
| 2009/0030412 A1 | 1/2009 | Willis et al. |
| 2009/0076409 A1 | 3/2009 | Wu et al. |
| 2009/0125010 A1 | 5/2009 | Sharkey et al. |
| 2009/0216220 A1 | 8/2009 | Hoey et al. |
| 2009/0306640 A1 | 12/2009 | Glaze et al. |
| 2010/0078046 A1 | 4/2010 | Labib et al. |
| 2010/0082021 A1 | 4/2010 | Gutierrez et al. |
| 2010/0094268 A1 | 4/2010 | Bouthillier et al. |
| 2010/0094270 A1 | 4/2010 | Sharma |
| 2010/0100091 A1 | 4/2010 | Truckai |
| 2010/0100094 A1 | 4/2010 | Truckai |
| 2010/0106152 A1 | 4/2010 | Truckai et al. |
| 2010/0114083 A1 | 5/2010 | Sharma |
| 2010/0114089 A1 | 5/2010 | Truckai et al. |
| 2010/0168731 A1 | 7/2010 | Wu et al. |
| 2010/0168739 A1 | 7/2010 | Wu et al. |
| 2010/0174282 A1 | 7/2010 | Demarais et al. |
| 2010/0179528 A1 | 7/2010 | Shadduck et al. |
| 2010/0204688 A1 | 8/2010 | Hoey et al. |
| 2010/0228222 A1 | 9/2010 | Williams et al. |
| 2010/0249773 A1 | 9/2010 | Clark et al. |
| 2010/0262133 A1 | 10/2010 | Hoey et al. |
| 2011/0009829 A1 | 1/2011 | Kosinski et al. |
| 2011/0054508 A1 | 3/2011 | Zhou et al. |
| 2011/0077628 A1 | 3/2011 | Hoey et al. |
| 2011/0112400 A1 | 5/2011 | Emery et al. |
| 2011/0112432 A1 | 5/2011 | Toth |
| 2011/0112433 A1 | 5/2011 | Toth |
| 2011/0112523 A1 | 5/2011 | Toth et al. |
| 2011/0118718 A1 | 5/2011 | Toth et al. |
| 2011/0118719 A1 | 5/2011 | Vissy et al. |
| 2011/0160648 A1 | 6/2011 | Hoey |
| 2011/0166499 A1 | 7/2011 | Demarais et al. |
| 2011/0178570 A1 | 7/2011 | Demarais |
| 2011/0200171 A1 | 8/2011 | Beetel et al. |
| 2011/0208096 A1 | 8/2011 | Demarais et al. |
| 2011/0208178 A1 | 8/2011 | Truckai |
| 2011/0257564 A1 | 10/2011 | Demarais et al. |
| 2011/0264011 A1 | 10/2011 | Wu et al. |
| 2011/0264075 A1 | 10/2011 | Leung et al. |
| 2011/0264090 A1 | 10/2011 | Shadduck et al. |
| 2012/0065632 A1 | 3/2012 | Shadduck |
| 2012/0101413 A1 | 4/2012 | Beetel et al. |
| 2012/0101538 A1 | 4/2012 | Ballakur et al. |
| 2012/0116382 A1 | 5/2012 | Ku et al. |
| 2012/0116383 A1 | 5/2012 | Mauch et al. |
| 2012/0116486 A1 | 5/2012 | Naga et al. |
| 2012/0130359 A1 | 5/2012 | Turovskiy |
| 2012/0130360 A1 | 5/2012 | Buckley et al. |
| 2012/0130458 A1 | 5/2012 | Ryba et al. |
| 2012/0136343 A1 | 5/2012 | Burnett |
| 2012/0136344 A1 | 5/2012 | Buckley et al. |
| 2012/0136350 A1 | 5/2012 | Goshgarian et al. |
| 2012/0136417 A1 | 5/2012 | Buckley et al. |
| 2012/0136418 A1 | 5/2012 | Buckley et al. |
| 2012/0143293 A1 | 6/2012 | Mauch et al. |
| 2012/0150267 A1 | 6/2012 | Buckley et al. |
| 2012/0158104 A1 | 6/2012 | Huynh et al. |
| 2012/0184949 A1 | 7/2012 | Gurskis et al. |
| 2012/0197198 A1 | 8/2012 | Demarais et al. |
| 2012/0197245 A1 | 8/2012 | Burnett et al. |
| 2012/0209281 A1 | 8/2012 | Truckai |
| 2012/0232545 A1 | 9/2012 | Truckai et al. |
| 2012/0245583 A1 | 9/2012 | Truckai et al. |
| 2012/0259271 A1 | 10/2012 | Shadduck et al. |
| 2012/0283717 A1 | 11/2012 | Sharkey et al. |
| 2013/0006231 A1 | 1/2013 | Sharma et al. |
| 2013/0116683 A1 | 5/2013 | Shadduck et al. |
| 2013/0237978 A1 | 9/2013 | Shadduck et al. |
| 2013/0261539 A1 | 10/2013 | King |
| 2013/0296837 A1 | 11/2013 | Burnett et al. |
| 2014/0031805 A1 | 1/2014 | Shadduck |
| 2014/0088575 A1 | 3/2014 | Loeb |
| 2014/0088581 A1 | 3/2014 | Kelly et al. |
| 2014/0200570 A1 | 7/2014 | Hoey et al. |
| 2015/0025515 A1 | 1/2015 | Hoey et al. |
| 2015/0335373 A1 | 11/2015 | Chee et al. |
| 2015/0335380 A1 | 11/2015 | Chee et al. |
| 2017/0354452 A1 | 12/2017 | Gurskis et al. |

(56) References Cited

U.S. PATENT DOCUMENTS

| | | |
|---|---|---|
| 2018/0168713 A1 | 6/2018 | Hoey et al. |
| 2018/0193079 A1 | 7/2018 | Hoey et al. |
| 2018/0289416 A1 | 10/2018 | Chee et al. |
| 2019/0117289 A1 | 4/2019 | Sharkey et al. |
| 2019/0117290 A1 | 4/2019 | Sharkey et al. |
| 2019/0142496 A1 | 5/2019 | Chee et al. |
| 2019/0216523 A1 | 7/2019 | Gurskis et al. |
| 2019/0223934 A1 | 7/2019 | Shadduck |

FOREIGN PATENT DOCUMENTS

| | | |
|---|---|---|
| CN | 102271602 A | 12/2011 |
| CN | 103717126 A | 4/2014 |
| CN | 104135960 A | 11/2014 |
| JP | H06-285074 A | 10/1994 |
| JP | 2000502585 A | 3/2000 |
| JP | 20003513742 A | 4/2003 |
| JP | 2010516351 A | 5/2010 |
| WO | WO98/57603 A1 | 12/1998 |
| WO | WO99/53853 A1 | 10/1999 |
| WO | WO00/011927 A2 | 3/2000 |
| WO | WO00/29055 A1 | 5/2000 |
| WO | WO01/85012 A2 | 11/2001 |
| WO | WO02/069821 A1 | 9/2002 |
| WO | WO 03/070302 A1 | 8/2003 |
| WO | WO2005/025635 A2 | 3/2005 |
| WO | WO2005/102175 A2 | 11/2005 |
| WO | WO2006/003665 A2 | 1/2006 |
| WO | WO 2006/055695 A1 | 5/2006 |
| WO | WO06/108974 A1 | 10/2006 |
| WO | WO2009/009398 A1 | 1/2009 |
| WO | WO2010/045055 A2 | 4/2010 |
| WO | WO2010/048007 A1 | 4/2010 |
| WO | WO2011/025658 A1 | 3/2011 |
| WO | WO2011/053599 A1 | 5/2011 |
| WO | WO2011/060189 A1 | 5/2011 |
| WO | WO2011/060191 A1 | 5/2011 |
| WO | WO2012/106260 A2 | 8/2012 |

OTHER PUBLICATIONS

Peliks et al.; U.S. Appl. No. 16/077,542 entitled "Methods and apparatus for determining the integrity of a bodily cavity," filed Aug. 13, 2018.

Hoey et al.; U.S. Appl. No. 15/918,962 entitled "Medical system and method of use," filed Mar. 12, 2018.

Fishman et. al.; A randomized trial comparing lung-volume-reduction surgery with medical therapy for severe emphysema; N Engl J Med; 348(210. pp. 2059-2073; May 22, 2003.

Homasson et. al.; Bronchoscopic cryotherapy for airway strictures caused by tumors; Chest; 90(2); pp. 159-164; Aug. 1, 1986.

Marasso et al.; Radiofrequency resection of bronchial tumours in combination with cryotherapy: evaluation of a new technique; Thorax; 53(2); pp. 106-109; Feb. 1998.

Marasso et. al.; Cryosurgery in bronchoscopic treatment of tracheobronchial stenosis; Cheat; 103(2); pp. 472-474; Feb. 1993.

Morice et. al; Endobronchial argon plasma coagulation for treatment of hemoptysis and neoplastic airway obstruction; Chest; 119(3); pp. 781-787; Mar. 1, 2001.

Tschirren et. al.; Intrathoracic airway trees: segmentation and airway morphology analysis from low-dose CT scans; IEEE Transactions on Medical Imaging; 24(12); pp. 1529-1539; Dec. 2005.

Unger et. al.; Monolithic Microfabricated Valves and Pumps by Multilayer Soft Lithography; Science, 288(5463); pp. 113-116; Apr. 7, 2000.

Van De Velde; Vapo-cauterization of the uterus; Amer. J. Med. Sci.; vol. CXVIII (118); Nov. 1899.

Blacker; Vaporization of the uterus; J. Obstet. & Gyn.; vol. 1; Issue 5; pp. 488-511; May 1902.

Neuwirth et al.; The endometrial ablator: a new instrument; Obst. & Gyn.; vol. 83; No. 5; part 1; pp. 792-796; May 1994.

Prior et al.; Treatment of mennorrhagia by radiofrequency heating; Int. J. Hyperthermia; vol. 7; No. 2; pp. 213-220; Mar.-Apr. 1991.

Baker et al.; Threshold intrauterine perfusion pressures for intraperitoneal spill during hydrotubation and correlation with tubal adhesive diseases; Fertility and Sterility; 64(6); pp. 1066-1069; Dec. 31, 1995.

Kim et al.; Polyurethanes having shape memory effect; Polymer-Letchworth; 37(26); pp. 5781-5793; Jan. 1996.

Poco; Industry news: Poco introduces improved CXT—CXT—xtra; 2 pages; retrieved from the internet (https://web.archive.org/web/20061215223908/http://www.poco.com/us/) on Feb. 2020.

Stanford; Capacitor micro machined ultrasonic transducer (cMUT); 10 pages; retrieved from the internet (https://web.archive.org/web/20040205083311/http://acoustics.stanford.edu/group/cmut1.pdf) on Feb. 20, 2020.

INTEGRITY TESTING METHOD AND APPARATUS FOR DELIVERING VAPOR TO THE UTERUS

CROSS REFERENCE TO RELATED APPLICATIONS

This application is a continuation of U.S. application Ser. No. 13/648,132, filed Oct. 9, 2012, now U.S. Pat. No. 9,662,060, which claims the benefit under 35 U.S.C. 119 of U.S. Provisional Patent Application No. 61/544,890, filed Oct. 7, 2011, titled "Integrity Testing Method and Apparatus for Delivering Vapor to the Uterus", both of which are incorporated herein by reference.

INCORPORATION BY REFERENCE

All publications and patent applications mentioned in this specification are herein incorporated by reference to the same extent as if each individual publication or patent application was specifically and individually indicated to be incorporated by reference.

FIELD

The present disclosure generally relates to uterine procedures incorporating a distension media such as a fluid or a gas that could be used with endoscopic procedures or other visualization systems such ultrasound or fluoroscopy. The present disclosure is particular suited for endometrial ablation of the uterine lining. More specifically, the present disclosure relates to endometrial ablation with a heated vapor.

BACKGROUND

Endometrial ablation (i.e., the removal or destruction of the endometrial lining of the uterus) is used as an alternative to hysterectomy for treating menorrhagia, or other uterine diseases. One prior technique for performing endometrial ablation employs a resectoscope (i.e., a hysteroscope with a built-in wire loop or other ablative devices) that is inserted transcervically into the uterus, and uses radio-frequency electrical current (RF current) to remove or coagulate the endometrial tissue. These standard techniques typically are performed in a hospital setting and importantly utilize hysteroscopy for visualization of the procedure while treating the uterine lining.

Some approaches make use of heated fluid to ablate the endometrium. For example, early journal articles describe the use of steam to treat uterine hemorrhage. The use of steam for this purpose was later discredited, apparently due to patient morbidity and mortality. See, e.g., Fuller U.S. Pat. No. 6,139,571. More recent descriptions of the use of injecting hot fluid into the uterus have been described. Uterine therapies employing a contained fluid have also been described.

In an effort to simplify the procedure, approaches have been developed that do not require concurrent hysteroscopic visualization. In practice, many of these techniques recommend that the physician or user employ hysteroscopy to visualize and inspect the uterine cavity prior to performing the endometrial ablation procedure. In addition, hysteroscopy may be employed at the conclusion of the endometrial ablation procedure as a method to inspect the uterine cavity post treatment. During this hysteroscopic inspection, the physician is verifying that the uterine cavity is not perforated although perforations may not be readily apparent even with hysteroscopic visualization. In general, a physician seeks to avoid perforations for many reasons including the potential for unintended injuries to neighboring organs and maintaining or confining the treatment area to specifically the uterine cavity in the case of endometrial ablation procedures.

Endometrial ablation techniques that do not require active hysteroscopic visualization during treatment operation are commonly referred to as "blind" techniques since the physician is using tactile feel, or markers and indicia on the endometrial ablation device to indicate proper placement of the device in the uterine cavity. One of these particular devices utilizes a balloon-based system using ultrasound as the energy source. High frequency, or radiofrequency (RF), energy has also been used to perform thermal ablation of endometrial tissue. Current products for performing endometrial ablation include the NOVASURE® procedure and a system marketed under the trade name THERMACHOICE®, by Ethicon, Inc. of Somerville, N.J. Cryogenic ablation, or "cryoablation," such as HER OPTION® from American Medical Systems, Inc., is another endometrial treatment approach. All of the products above are characterized as "blind" or not requiring direct hysteroscopic visualization during the treatment.

In utilizing an endometrial ablation technology that does not require hysteroscopic visualization, it would be beneficial to employ a test to verify that the uterine cavity is intact or unperforated prior to performing the treatment. Such tests are referred to as uterine integrity tests and these tests can be performed with endometrial ablation procedures and any procedure of the uterus or hollow body cavity or organ. In addition, these tests can be used with hysteroscopic procedures since a perforation may not be readily detected even under direct vision.

Integrity tests employ saline or gas, preferably carbon dioxide gas, as agents to verify if the uterine cavity is intact in regards to holding fluid or gas pressure. The gas or fluid is supplied under pressure to the uterine cavity and a leak in the uterine cavity, whether it is a perforation, an unsealed cervical canal, or the effect of excess fluid exiting the fallopian tubes, can be discerned. Stern et al. (U.S. Pat. No. 5,562,720) and Sampson et al. (U.S. Pat. Nos. 6,554,780, 6,743,184, 6,872,183, and 7,063,670) describe such pressure techniques while other approaches check for fluid imbalances between an input source and output collection using volume measurements. Other approaches mention using flow rate and pressure measurements.

In practice, it would be beneficial to the physician to have an indicator of the proper location of the endometrial treatment device during "blind" procedures.

During integrity testing, it would be beneficial if the uterine contractions did not impact the readings or interpretation of the integrity test.

SUMMARY OF THE DISCLOSURE

In some embodiments, a method of performing a procedure on a uterus of a patient is provided, comprising performing a uterine integrity test comprising inserting a uterine device into the uterus of the patient, delivering gas or fluid from an inflow lumen of the uterine device into the uterus, measuring a flow rate of the gas or fluid as it is delivered into the uterus, determining that the uterus is sealed if the flow rate decreases below a flow rate threshold value, and after performing the uterine integrity test and determining that the uterus is sealed, performing a patency test for the uterine device comprising delivering gas or fluid from the inflow lumen of the uterine device into the uterus, removing gas or fluid from the uterus with an outflow lumen of the uterine device, determining that the uterine device is not clogged or embedded in tissue if a flow rate of gas or fluid is observed in the outflow lumen of the uterine device.

In one embodiment, the uterine device is a uterine ablation device.

In another embodiment, fluid flow is observed in a flow meter of the outflow lumen.

In some embodiments, the determining that the uterus is sealed step further comprises determining that the uterus is sealed if the flow rate decreases below a flow rate threshold value within a predetermined time period.

In particular embodiments, a one way valve in the inflow lumen of the uterine device reduces or eliminates retrograde flow from the uterus back through the uterine device. In one embodiment, the one way valve prevents retrograde flow and sinusoidal wave forms in response to uterine contractions.

In some embodiments, the determining that the uterus is sealed step further comprises determining that the uterus is sealed if the flow rate decreases to zero after the predetermined time period.

In one embodiment, the delivering steps further comprise delivering gas or fluid from the inflow lumen of the uterine device into the uterus at a constant pressure bounded by a safety threshold pressure. In some embodiments, the safety threshold pressure is approximately 70 mm Hg.

In some embodiments, the flow rate threshold value is between 2 and 5 ml/min.

In one embodiment the method further comprises, during the patency test, determining that the uterine device is clogged or embedded in tissue if the return flow of gas or fluid is not observed in the outflow lumen of the uterine device.

In some embodiments, the method further comprises, during the uterine integrity test, determining that the uterus has a perforation that is sealed at lower pressures and is opened at higher pressures if the flow rate oscillates between a low level and a high level.

In additional embodiments, during the uterine integrity test, the determining that a uterus is sealed step further comprises determining that the uterus is sealed if the flow rate averages approximately zero or the flow rate average is below a threshold value over a predetermined time period.

In some embodiments, the method further comprises, after determining that the uterus is sealed and that the uterine ablation device is not clogged or embedded in tissue, delivering a heated condensable vapor to the uterus to ablate uterine tissue.

In one embodiment the method further comprises assessing a volume of gas or fluid delivered in the integrity test to estimate a size of the uterus.

In additional embodiments, the method further comprises assessing a volume of gas or fluid delivered in the integrity test to estimate a location of a distal tip of the uterine device within the uterus.

Some embodiments further comprise assessing a flow rate of gas or fluid delivered in the integrity test to estimate a location of a distal tip of the uterine device within the uterus. In other embodiments, assessing the volume indicates that the distal tip is in a false passage. Additional embodiments comprise assessing the flow rate indicates that the distal tip is in a false passage. In some embodiments, assessing the volume indicates that the distal tip is in the patient's peritoneal cavity. In other embodiments, assessing the flow rate indicates that the distal tip is in the patient's peritoneal cavity.

In one embodiment, the delivering gas or fluid step of the uterine integrity test further comprises delivering gas or fluid from inflow and outflow lumens of the uterine device to the uterus.

In another embodiment, the performing a uterine integrity test step further comprises removing gas or fluid from the uterus with an outflow lumen of the uterine ablation device, measuring an outflow flow rate of gas or fluid in the outflow lumen, and comparing the flow rate of gas or fluid delivered into the uterus to the outflow flow rate of gas or fluid in the outflow lumen to provide a dynamic measurement for the presence of leaks in the uterus.

In some embodiments, the removing gas or fluid step of the patency test further comprises removing gas or fluid from the uterus with an outflow lumen of the uterine device positioned distally from the inflow lumen of the uterine device.

In another embodiment, the delivery step is automatically initiated by module controller of the uterine ablation device.

Another method of performing a patency test for a uterine ablation device is provided, comprising inserting the uterine ablation device into a uterus of a patient, delivering gas or fluid from an inflow lumen of the uterine ablation device into the uterus, removing gas or fluid from the uterus with an outflow lumen of the uterine ablation device, and determining that the uterine ablation device is not clogged or embedded in tissue if a return flow of gas or fluid is observed in the outflow lumen of the uterine ablation device.

A method of performing a procedure on a uterus of a patient is also provided, comprising performing a uterine integrity test comprising inserting a uterine ablation device into the uterus of the patient, delivering gas or fluid from an inflow lumen of the uterine ablation device into the uterus, measuring a flow rate of the gas or fluid as it is delivered into the uterus, determining that the uterus is sealed if the flow rate decreases below a flow rate threshold value, and after performing the uterine integrity test and determining that the uterus is sealed, monitoring changes in intrauterine pressure to determine if contractions are occurring.

In some embodiments, a method of performing a procedure on a uterus of a patient comprises performing a uterine integrity test comprising inserting a uterine ablation device into the uterus of the patient, delivering gas or fluid from an inflow lumen of the uterine ablation device into the uterus measuring a flow rate of the gas or fluid as it is delivered into the uterus, determining that the uterus is sealed if the flow rate decreases below a flow rate threshold value, and eliminating retrograde flow through the inflow lumen with a one way valve in response to uterine contractions.

In some embodiments, the one way valve reduces noise in a flow meter of the inflow lumen caused by uterine contractions or relaxations, movements by the patient, or manipulations of the patient or inflow lumen by the physician or medical staff.

A method of performing a procedure on a uterus of a patient is provided, comprising performing a uterine integrity test comprising inserting a uterine device into the uterus of the patient, delivering a fluid from an inflow lumen of the uterine device into the uterus, measuring a delivery flow rate of the fluid as it is delivered into the uterus, determining that the uterus is sealed if the flow rate decreases below a flow rate threshold value, and providing fluid at a known flow rate to the uterus with the uterine device, diverting the fluid through a known orifice proximal to the uterine device, and measuring a diversion flow rate that is diverted to assess the integrity of the uterine cavity.

In some embodiments, the uterine device is a uterine ablation device.

A method of performing a procedure on a uterus of a patient is provided, comprising inserting a uterine ablation device into the uterus of the patient, delivering gas or fluid from an inflow lumen of the uterine ablation device into the uterus, measuring a flow rate of the gas or fluid as it is delivered into the uterus, distending the uterus with the delivered gas or fluid, determining that the uterus is sealed if the flow rate decreases below a flow rate threshold value, eliminating retrograde flow through the inflow lumen with a one way valve in response to uterine contractions, determining that the uterine ablation device is not clogged or embedded in tissue if a return flow of gas or fluid is observed in an outflow lumen of the uterine ablation device, treating the uterus of the patient without reducing distension pressure with the uterine ablation device immediately following the step of determining that the uterine ablation device is not clogged and the uterus is sealed.

In one embodiment, a method of performing a procedure on a uterus of a patient, comprises inserting a uterine ablation device into the uterus of the patient, delivering gas or fluid from an inflow lumen of the uterine ablation device into the uterus, measuring a flow rate of the gas or fluid as it is delivered into the uterus, distending the uterus with the flow of gas or fluid, determining that the uterus is sealed if the flow rate decreases below a flow rate threshold value, eliminating retrograde flow through the inflow lumen with a one way valve in response to uterine contractions, determining that the uterine ablation device is not clogged or embedded in tissue if a return flow of gas or fluid is observed in the outflow lumen of the uterine ablation device, and treating the uterus of the patient with the uterine ablation device immediately following the step of determining that the uterine ablation device is not clogged and the uterus is sealed without reducing distension pressure in the uterus of the patient.

A uterine treatment device is provided, comprising a shaft sized and configured for insertion into a uterus of a patient, inflow and outflow lumens disposed along a length of the shaft, at least one inflow port disposed at a distal end of the inflow lumen, at least one outflow port disposed at a distal end of the outflow lumen, a gas/fluid source operatively coupled to the inflow and outflow lumens, at least one flow meter disposed between the gas/fluid source and the shaft, and a controller configured deliver gas or fluid from the gas/fluid source through the inflow lumen into the uterus, detect with the at least one flow meter an integrity flow rate of gas or fluid as it is delivered into the uterus, and determine that the uterus is sealed if the integrity flow rate decreases below an integrity flow rate threshold value, the controller also configured to, if it is determined that the uterus is sealed, deliver gas or fluid through the inflow lumen into the uterus, remove gas or fluid from the uterus with the outflow lumen, detect with the at least one flow meter a patency flow rate of gas or fluid, and determine that the uterine treatment device is not clogged or embedded in tissue based on the patency flow rate.

In one embodiment, a uterine treatment device comprises a shaft sized and configured for insertion into a uterus of a patient, inflow and outflow lumens disposed along a length of the shaft, at least one inflow port disposed at a distal end of the inflow lumen, at least one outflow port disposed at a distal end of the outflow lumen, a gas/fluid source operatively coupled to the inflow and outflow lumens, at least one flow meter disposed between the gas/fluid source and the shaft, and a controller configured to perform a uterine integrity test by allowing gas or fluid to flow from the gas/fluid source into the uterus without allowing for gas or fluid to be removed from the uterus and monitoring an integrity flow rate of gas or fluid measured by the at least one flow meter, the controller being further configured to perform a patency test by allowing gas or fluid to flow from the gas/fluid source into the uterus, removing the gas or fluid from the uterus, and monitoring a patency flow rate of gas or fluid measured by the at least one flow meter.

In some embodiments, the device further comprises a first valve disposed between the gas/fluid source and the inflow lumen, a second valve disposed between the gas/fluid source and the outflow lumen, wherein the controller is configured to perform the uterine integrity test by opening the first valve and closing the second valve, wherein the controller is configured to perform the patency test by opening the first and second valves.

In other embodiments, the device further comprises a first valve disposed between the gas/fluid source and the inflow lumen, second and third valves disposed between the gas/fluid source and the outflow lumen, wherein the controller is configured to perform the uterine integrity test by opening the first and second valves and closing the third valve to allow gas or fluid to flow into the uterus through both the inflow and outflow lumens, wherein the controller is configured to perform the patency test by opening the first and third valves and closing the second valve to allow gas or fluid to flow into the uterus through the inflow lumen and to remove gas or fluid from the uterus through the outflow lumen.

DETAILED DESCRIPTION

Figure 1A:
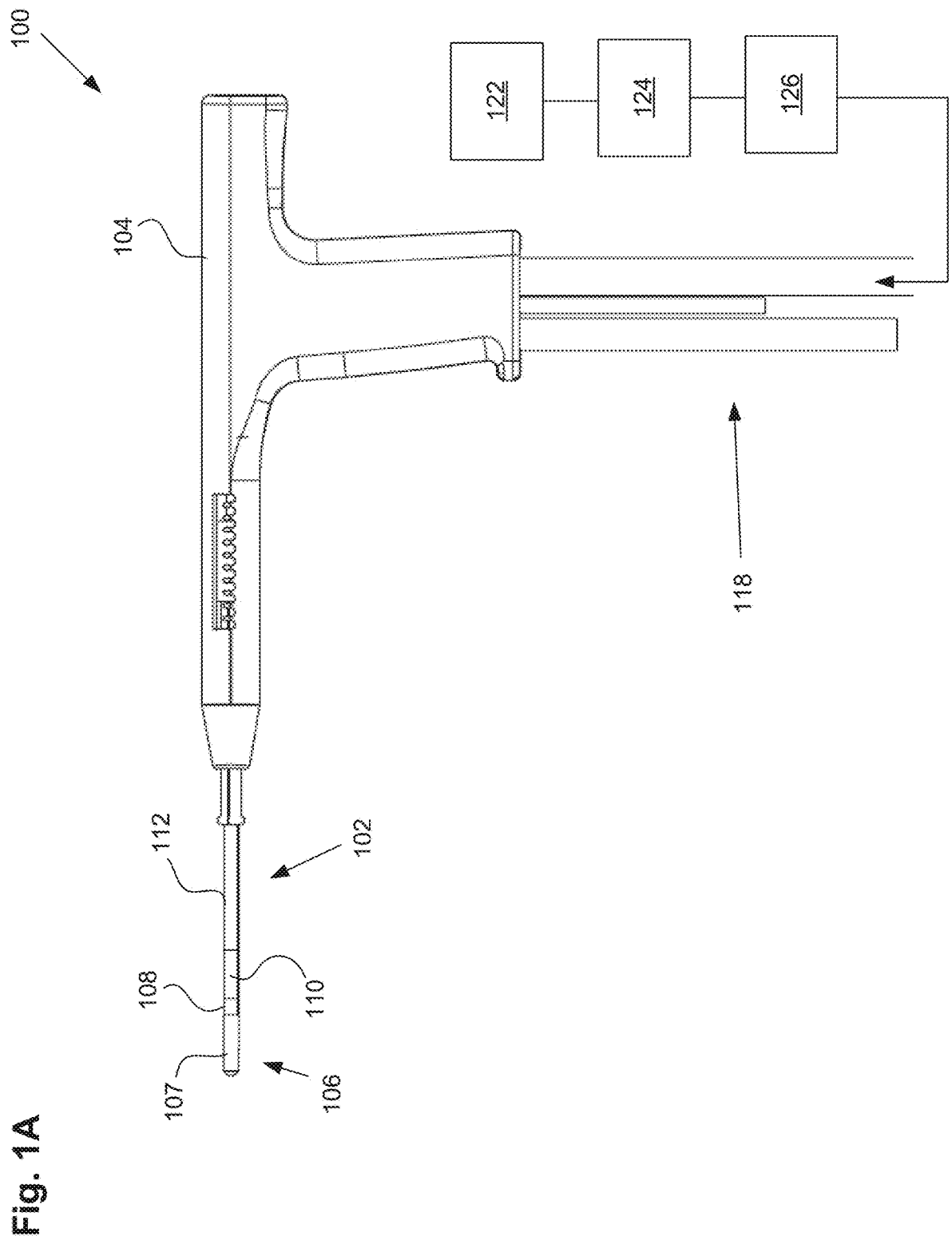
FIGS. 1A-1B illustrate one embodiment of a uterine ablation device.

FIG. 1A illustrates a uterine ablation device 100 sized and configured to access the endometrium of a uterus and to deliver a heated vapor to the uterus to ablate uterine tissue. The device can be configured to ablate and treat the endometrial lining of the uterus as an alternative to hysterectomy for treating menorrhagia or other uterine diseases. In some embodiments, the device 100 can be configured to gain access to the uterus by being inserted through a cannula or hysteroscope. The device 100 can include shaft 102, handle 104, distal tip 106, vapor ports 107, distal anchor or distal balloon 108, central or sealing balloon 110, proximal or positioning balloon 112, and connection lumens 118, which can couple the uterine ablation device to a control system (not shown) comprising a computer, a vapor generation system, and mechanisms configured to inflate and deflate the balloons as well as control the delivery and removal of integrity gas/fluid and vapor from the device. Additionally, connection lumens 118 can connect device 100 to a gas/fluid source 122, pressure regulator 124, and flow meter(s) 126. Vapor ports 107 near the distal tip 106 of the device can be fluidly coupled to the connection lumens 118 via inflow and outflow lumens (not shown). The vapor ports, inflow and outflow lumens, connection lumens, gas/fluid source, pressure regulator, and flow meters can be configured for testing the integrity of the patient's uterus, proper placement of the device, and verifying the presence of flow between the inflow and outflow lumens of the device.

The flow meter can be any flow meter as known in the art, including a thermal mass flow meter, an ultrasonic flow meter, a paddlewheel, or a variable area flow meter. In one embodiment, an ultrasonic flow meter that utilizes transit time and Doppler flow readings is advantageous since it is a non-contact system that does not need to physically interact with the fluid or gas media being employed in the integrity test. An ultrasonic flow meter can be easily adaptable to the exterior dimensions of an inflow lumen. In addition, a drip chamber within the inflow lumen can be used to manually visualize or record drips or flow from the fluid source as the integrity test indicates a sealed uterine cavity. In some uterine procedures, it may be advantageous to use other types of fluid besides saline including Lactated Ringers, non-isotonic solutions for certain electrosurgical procedures, gels, foams, fluids of varying viscosity for some ultrasonographic procedures, or other fluids used in uterine procedures.

In one embodiment, a one way valve can be placed in the inflow lumen just distal or past the flow meter from the gas/fluid source. The one way valve can allow for the flow of gas/fluid (e.g., saline) from the gas/fluid source to the device and uterine cavity. The one way should not interfere with the operation of the flow meter and its readings. In operation, the uterine cavity is a muscle that can undergo significant contractions in the presence of uterine distension or when the uterine cavity is filled with gas/fluid, and in particular a fluid such as saline. These contractions can push the fluid retrograde back through the saline lumen and past the flow meter. In doing so, flow meter measurements can become difficult to interpret or may produce sinusoidal waves in the output readings. The placement of the one way valve in this location can eliminate retrograde fluid flow and stabilize readings for the flow meter during episodes of uterine contractions.

Handle 104 can be an ergonomic handle and can include features and controls for using the device (e.g., buttons, levers, indicia for providing feedback for depths of insertion, valves, etc), including features for controlling inflation of balloons 108, 110, and 112, and for controlling the delivery and removal of integrity test gas/fluid and heated vapor from the device. The handle can also include features and controls for testing the integrity of the patient's uterus, proper placement of the device and verifying the presence of flow between the inflow and outflow lumens of the device.

The balloons described herein can be any type of flexible balloon, such as rubber, latex, urethane, silicone, PET, LDPE, parylene, nylon, PE, combinations of these polymers, or can be manufactured from any other suitable material as known in the art. It should be noted that in some embodiments, the distal anchor comprises a balloon, but in other embodiments, the distal anchor comprises an expandable anchor or expansion mechanism, such as expandable frames, filters, nets, or cages, or non-expandable components that increase the diameter of the shaft of the uterine ablation device. For purposes of this disclosure, however, the distal anchor may be referred to as a distal anchor or as a distal balloon.

Shaft 102 can be configured to deliver a heated vapor from a remote boiler (not shown) through the device and out of vapor ports 107 in distal tip 106. The shaft can also be configured to return vapor that has exited the device, including bodily fluids, uterine materials, and condensate back through the vapor ports and into the shaft. In FIG. 1A, vapor ports 107 are illustrated as including both the vapor delivery and vapor return ports. However, in other embodiments, the vapor delivery ports can be separate and distinct from the vapor return ports. For example, vapor delivery ports are intended to provide an even distribution of heated vapor through a cavity, and may comprise small lumens or holes on the end of the shaft. The vapor return ports, in contrast, are intended to return used vapor and condensate, and may comprise larger slots to prevent blood, tissue, etc from blocking or clogging the return lumen. The device comprises inflow and outflow gas and/or fluid delivery channels to conduct uterine integrity and patency tests. In some embodiments, the lumens to deliver and return vapor are the same as the channels to deliver and return gas and/or fluid for the uterine integrity and patency tests.

Referring still to FIG. 1A, uterine ablation device 100 is shown in a collapsed delivery configuration, with distal balloon 108, sealing balloon 110, and positioning balloon 112 deflated to reduce the cross sectional diameter of the device and can be 6 mm in diameter during insertion or smaller. When the device is in the delivery configuration, the reduced profile allows for easier access to through the vagina, cervical canal, and cervix to gain access to the uterus, and provides reduced patient discomfort during insertion. In some embodiments, the outer dimensions of the uterine ablation device are such that introduction of the device into the uterine cavity can be achieved without the need for mechanical or pharmacological dilation of the os prior to device introduction.

Figure 1B:
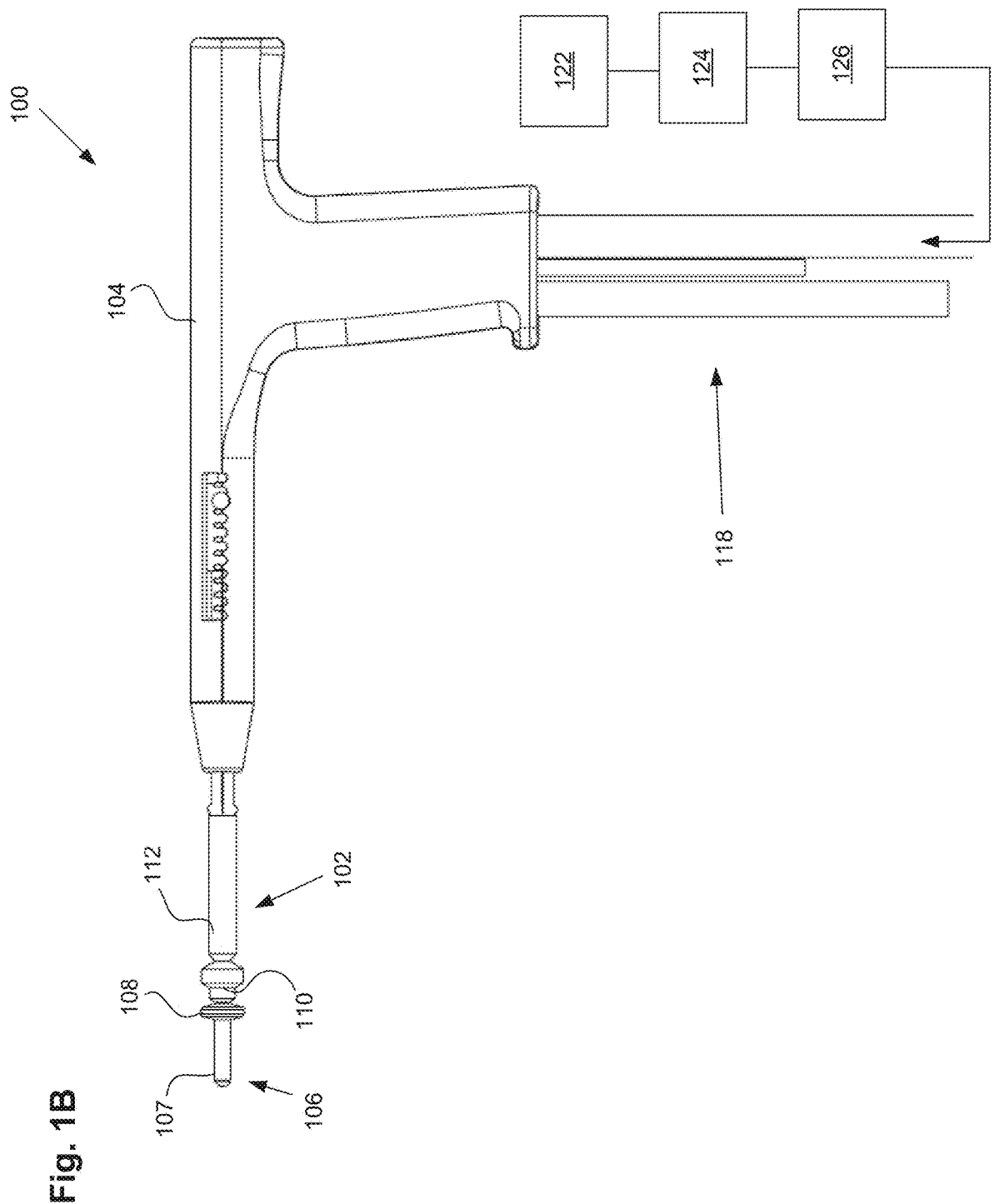

FIG. 1B illustrates the uterine ablation device 100 of FIG. 1A with all three balloons inflated, including distal balloon 108, central sealing balloon 110, and positioning balloon 112. The central balloon can be inflated with a fluid, such as saline, or alternatively, can be inflated with air. Although three balloons are depicted in FIG. 1B, in other variations one, two, four, or more balloons may be provided, and other balloon shapes may be used. The positioning balloon can be inflated with a room temperature medium, a cooled medium, or alternatively, a heated medium. In some embodiments, the central sealing balloon comprises a length along shaft 102 of approximately 15 mm to 25 mm. The central balloon can be disposed on the shaft between the distal balloon or anchor and the proximal balloon. In some embodiments, the central balloon is adjacent to both the distal balloon and the proximal balloon. In other embodiments, there is a small gap or space between one or more of the balloons. The length and position of the central balloon on the shaft ensures that when inflated, the central balloon seals the cervix off from the uterus near the internal os, but the balloon does not extend into the uterus or into the vagina of the patient. The central and proximal balloons can comprise any diameter, but preferably should have a diameter large enough to be able to engage the walls of the cervix and/or the vagina in the average female patient. For instance, the central balloon may have an inflated outer diameter of 10 mm and accommodate 9.5 psi of pressure in actual use. The proximal balloon can have a larger diameter, such as 17 mm and a lower inflation pressure of 7 psi.

Placement of the ablation device of FIGS. 1A-1B will now be described. The distal tip of the ablation device can be inserted past an external os into the cervical canal of the patient, and past an internal os of the patient to gain access to the uterus. In one embodiment, the distal balloon can be positioned within the uterus distal to the internal os, the sealing balloon can be positioned at or proximal to the internal os and extending into the cervical canal, and the positioning balloon can be positioned within the cervical canal and extending proximally into or towards the vagina.

Once the distal tip of the ablation device is disposed within the uterus, just distal to the internal os, the distal balloon can be inflated to the desired pressure. In some embodiments, the balloon can be inflated to a pressure of up to approximately 20 to 30 psi so as to prevent accidental withdrawal of the ablation device from the uterus. It should be noted that at this point, the distal balloon is positioned slightly past the internal os of the cervix. Inflation of the distal balloon can later serve as an anchor to prevent the device from sliding proximally out of the uterus.

Figure 2:
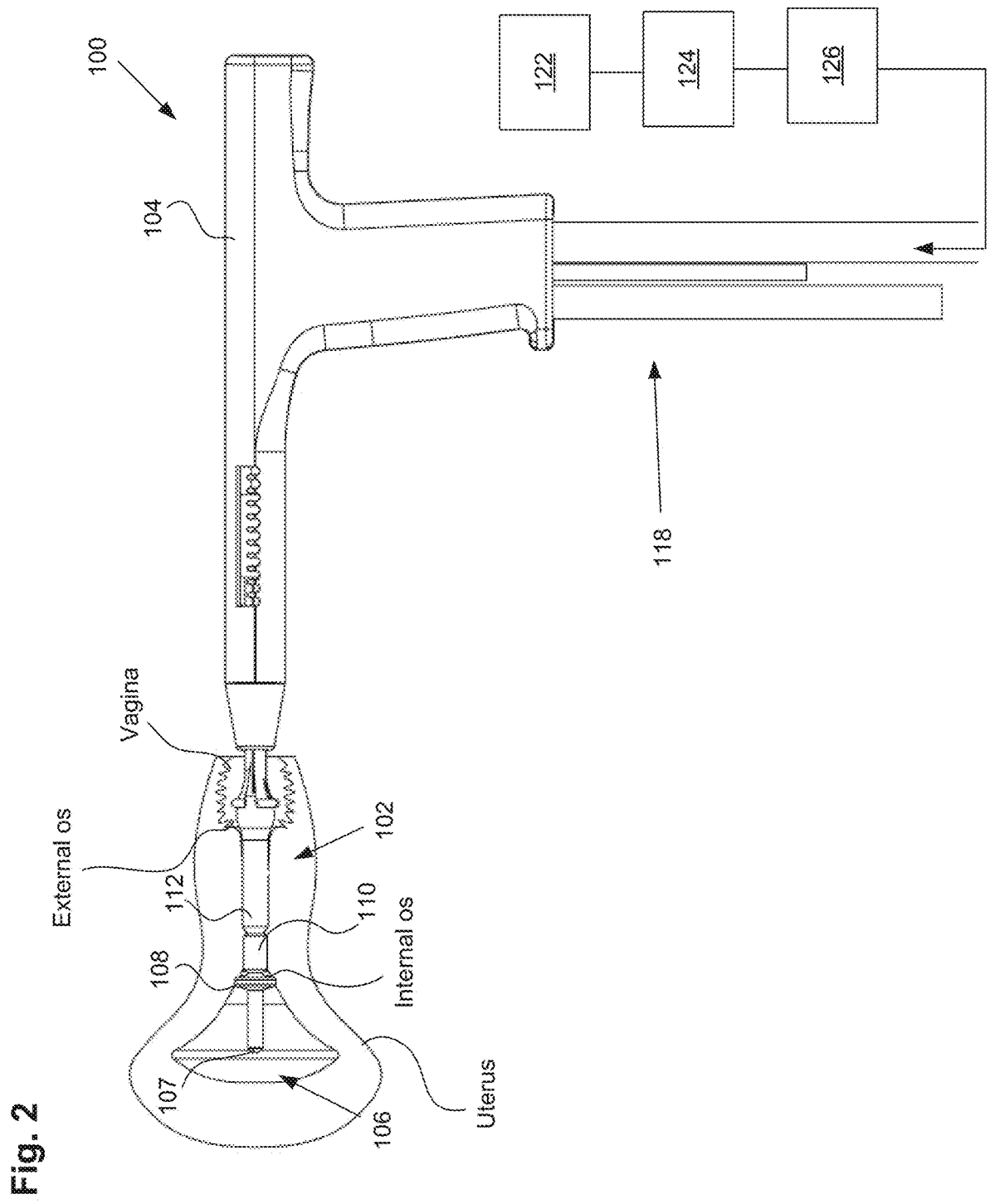
FIG. 2 illustrates an integrity test of the uterine ablation device.

After inflating the distal balloon, the proximal balloon can be inflated to cause the device to assume a positioned configuration, with the distal balloon fully seated against the internal os and the positioning or proximal balloon expanded within the cervix and extending past the external os into the vagina. As the proximal balloon is inflated, the balloon can expand outwardly from the cervix into the relatively unconstrained space of the vagina, which creates a compression force that pulls the device and the distal balloon proximally to engage against the interior portion of the internal os (also known as the cervical ostium or cervical os). FIG. 2 illustrates ablation device 100 inserted into the uterus of a patient with balloons 108, 110, and 112 inflated as described above.

After positioning the ablation device but prior to delivery of vapor, it can be advantageous to assess the integrity of the uterus to test that the vapor delivery tip of the device is positioned within a sealed uterus and to test that there is flow between the inflow and outflow lumens, by performing an integrity test and a patency test. The amount of fluid and rate in which it flows into the uterine cavity can provide the physician an indication of the size of the uterine cavity and whether the device is in a false passage. An integrity test can asses that the uterus is sealed, and determine leaks originating from 1) perforations to the uterine wall, or 2) leaks from inadequate sealing at the cervix or leaks from the fallopian tubes.

A second test that made an assessment for patency, referred to as the device lumens patency test or patency test, could provide an indication to the physician whether the device was clogged with debris or within a false passage. This additional information to the physician, in conjunction with the integrity test, could provide greater assurance to the physician of device location during "blind" endometrial ablation procedures.

In clinical use, a uterine integrity and patency test could be useful for additional uterine procedures besides uterine ablation procedures such as the implantation of a device, implant, or a diagnostic or therapeutic agent. In these cases, a separate unit or module that can conduct a uterine integrity and patency test, sequentially, separately, or individually, with a separate uterine cavity introducer can be employed without a uterine ablation device or system.

In one embodiment, a uterine integrity test can contain the following elements and steps. Referring to FIGS. 1A-1B and FIG. 2, gas/fluid source 122 can be connected to pressure regulator 124 comprising either one regulator or an additional back pressure regulator. The gas/fluid source can contain a gas, such as $CO_2$, or inert gases, or a fluid, such as saline, Ringer's Lactate, non-isotonic solutions, glycerine, and mineral oil for example. The regulator 124 is configured to keep the pressure of the external gas source below a safety threshold value. In one embodiment, the safety threshold value can be approximately 70 mm Hg. The actual pressure amount or graduation may not be monitored and may not need to be. The fluid or gas from gas/fluid source 122 can be driven at a constant pressure bounded by the safety threshold value (e.g., can be bounded by the maximum pressure the uterus will see during treatment, such as 70 mm Hg). In addition, it can be useful to operate a uterine integrity test at a pressure equal to higher than the pressure required for conducting the endometrial ablation or other uterine procedure.

In use, gas/fluid pressure can be achieved by elevating the gas/fluid source a height distance above the uterine cavity to create pressure. This height elevation can be verified by a measuring stick, tape or laser. An example of a clinically used height for a saline bag would be 32 inches above the height of a patient's uterus. At this height, the pressure would be between 50 and 70 mm Hg. This pressure is low enough to be below the reported opening pressure of the fallopian tubes. In addition, a pressure sensor within the uterine cavity can verify that the appropriate amount of pressure is being applied for the integrity test and patency tests. A self-adjusting feedback mechanism can be employed to raise or lower the pressure of the saline source in response to pressure measurements taken from within the uterine cavity. As an example, this feedback mechanism can raise or lower the height of the saline source in response to the pressure measurements taken from within the uterine cavity.

Alternatively, the uterine integrity test can be conducted by detecting a flow rate of the distal lumen of the uterine device or uterine ablation device under known conditions to determine the proper pressure or height of the gas/fluid source. For instance, flow rate readings can be taken while the gas/fluid source is at a certain height and the uterine device maintained within a known condition or in free space. As the height of the gas/fluid source is raised or lowered, the flow rate of the gas/fluid will respond accordingly until the gas/fluid source is placed at a height at the desired flow rate, or is pressurized to the desired amount. Likewise, the gas/fluid source can be raised or lowered by a self-adjusting feedback mechanism in response to the measured flow rate.

In some embodiments, the uterine ablation device can further include a flow meter 126 having a read out mechanism (not shown) to the end user. In some embodiments, the flow meter is disposed near distal tip 106 of the device. In other embodiments, the flow meter can be disposed within an outflow lumen of the device (not shown). In yet another embodiment, the flow meter can be disposed external to the device but along the flow path between gas/fluid source 122 and the ablation device. The flow meter can be configured to measure and report a flow rate of fluid/gas or vapor through the uterine ablation device. The read out mechanism can be numerical, graphical, or icon based. Other variations include various audio and visual signals, indicia, qualitative indicia, alarms, and color identifiers. A filter may or may not be attached to the flow meter.

Figure 3:
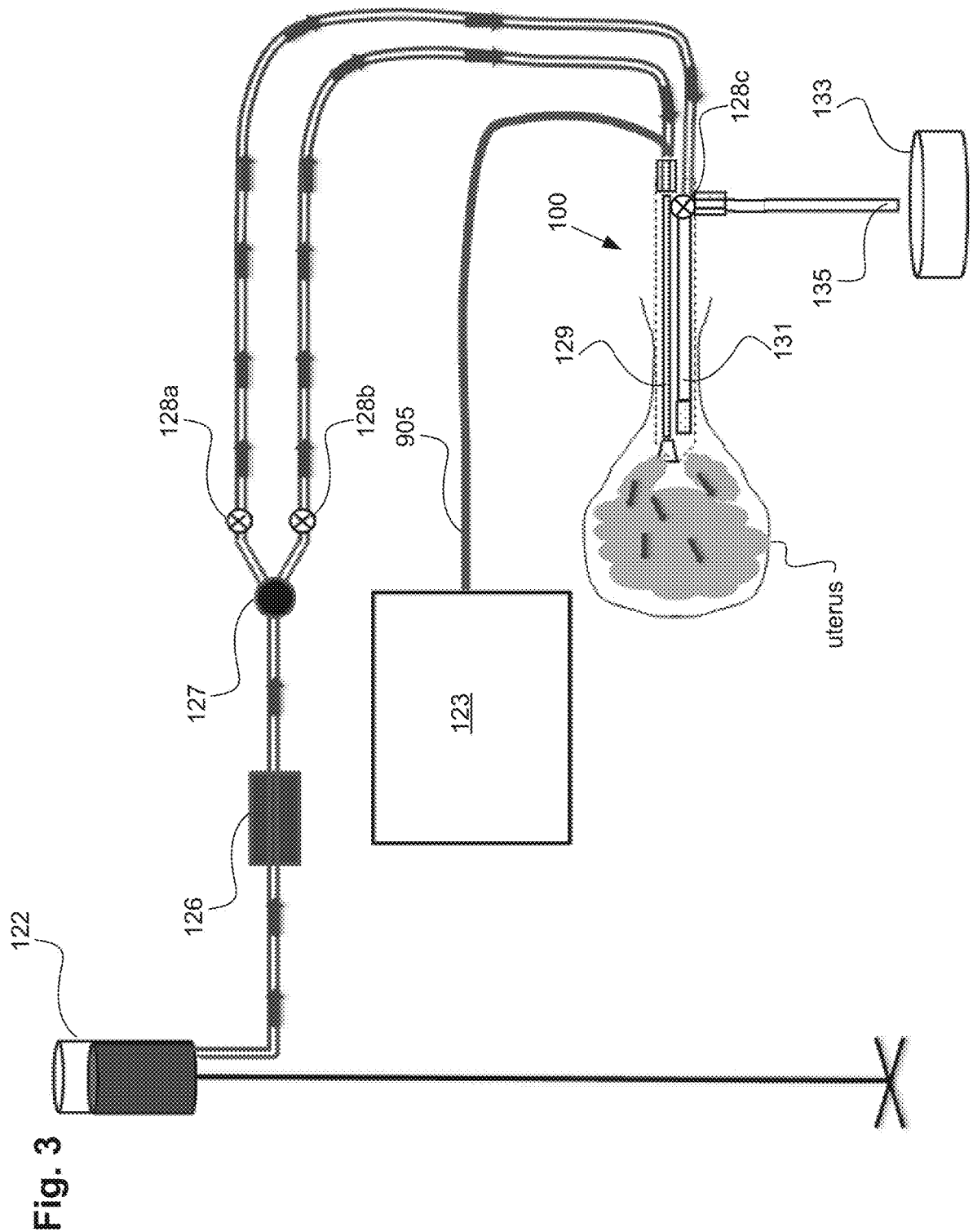
FIG. 3 illustrates one configuration of an apparatus during a uterine integrity test.

Referring to FIGS. 2 and 3, to perform a uterine integrity test, gas, such as $CO_2$, or a fluid, such as saline, can be delivered from the gas/fluid source 122, through the pressure regulator 124, and through the flow meter 126 into the uterine ablation device 100. As shown in FIG. 3, the gas/fluid can be delivered into the uterus via both inflow lumen 129 and outflow lumen 131.

In one embodiment, a one way valve 127 as seen in FIG. 3 can be located between the flow meter 126 and the uterine ablation device 100. In other variations the one way valve 127 can be located in the handle of the uterine ablation device 100 as well as other components such as the flow meter 126 and valves 903. The one way valve can reduce or eliminate retrograde flow of saline during uterine contractions. The one way valve is characterized as providing low resistance to flow in one direction (towards the uterine cavity) and high resistance to flow in the retrograde direction (towards the gas/fluid source). Advantageously the one way valve can stabilize flow values because retrograde flow values are eliminated. By reducing the sinusoidal wave patterns that can be caused by uterine contractions or relaxations, movements by the patient, or inadvertent manipulations of the inflow line or the patient herself by the physician or medical staff, the procedure time is reduced. This filtering out of negative flow values isolates positive components of flow, reduces noise in flow rate values, thereby accelerating the interpretation of flow rate data and reducing procedural time.

A controller of the uterine ablation device (not shown) can be configured to open and close valves 128a, 128b, and 128c to allow gas or fluid to flow from source 122 into the inflow and outflow lumens 129 and 131 of the ablation device 100. During a uterine integrity test, the controller can be configured to open valves 128a and 128b and close valve 128c. This allows gas or fluid to flow from source 122, through flow meter 126, through one way valve 127 and valves 127a and 128b, and into inflow lumen 129 and outflow lumen 131. As the gas or fluid enters the uterus, the flow meter can measure an integrity flow rate of the gas or fluid. If the flow rate decreases below an integrity flow rate threshold value, the controller can determine that the uterus is sealed. In some embodiments, this integrity flow rate threshold value can be approximately 5 ml/min.

The gas/fluid can exit vapor ports 107 of the device and enter the uterine cavity. These exit vapor ports can also be referred to as the fluid infusion tip and fluid outflow tip. As described above, for the integrity test, both the inflow and outflow lumens of the uterine ablation device can be utilized to provide fluid/gas to the uterine cavity. As the pressure in the uterus increases, the flow of fluid or gas through the uterine ablation device should decrease to a value of zero or to a value below an integrity flow rate threshold value, which occurs when the pressure in the uterus equals the drive pressure of the system. Utilizing both the inflow and outflow lumens for the flow of the gas/fluid during insertion of the device into the patient can help prevent the vapor ports from becoming clogged or blocked during insertion.

For the patency test, the inflow lumen can be utilized for gas/fluid flow into the uterus while the outflow lumen is used for the return of gas/fluid from the uterus.

For the integrity test, by measuring the flow of gas or fluid into the uterus with flow meter 126, and more specifically, by measuring a declining flow rate of gas/fluid into the uterus or a steady state flow rate in the uterus, the system or a user can determine the state of the uterus and correct positioning of the device in the uterus. For example, 1) if the flow rate does not decrease or decreases to a flow rate higher than a threshold flow rate, for example 5 ml/min, then there is either a leak in the uterus or the device, or the device is not positioned properly within the uterus; 2) if the flow rate drops to zero immediately, then the distal tip of the uterine ablation device may be clogged or embedded in the tissue; 3) if the flow rate drops to a level above zero and stays there (e.g., ~30 mL/min), then a small leak may be present. The size of the leak can be proportional to the measured flow rate; 4) if the flow rate oscillates between a low level and a high level, then a hole or leak may be present which is sealed or closed at lower pressures but opens at higher pressures; and 5) if the flow rate drops below a threshold value or to zero within a certain time limit, bounded by both min and max time, then the device is positioned correctly within a sealed uterus. In one embodiment, a min and max time to determine proper positioning within a sealed uterus can occur within a test window of 10 to 60 seconds with a 15 second window being preferred. The flow rate threshold can be set at a numerical value of 5 ml/min wherein flow rates dropping below 5 ml/min within the time window can be used as the threshold for a sealed uterine cavity and greater than or equal to 5 ml/min as the threshold for detecting a leak or an unsealed uterine cavity. The numerical value of 5 ml/min as a sealed or unsealed threshold for integrity testing has been shown to be effective for the uterine ablation device utilizing vapor. Intentionally made perforations in test uteri were demonstrated to not allow vapor to traverse the perforation at values less than 5 ml/min. The establishment of a threshold value for sealed or unsealed uterine cavity must take into account the resolution limitations of the flow sensors and meters, and the rate of saline absorption in the uterine cavity.

In analyzing integrity test data for leak or non-intact thresholds, empirical testing demonstrated that there is a statistically significant difference between tests determined as "pass" (flow<5 ml/min) or "fail" (flow>5 ml/min). The average minimum change in saline flow rate and maximum saline flow rate are significantly different, indicating that the integrity test can effectively discern between leaks and absence of leaks in a test environment where perforations are intentionally applied to a test uterine cavity as shown in the table below. This statistically significant difference improves further when negative flow values are eliminated with the use of a one way valve ($p<0.001$ for Min $\Delta$ flow and $p<0.001$ for Max flow). Based on this analysis, a 5 ml/min integrity test threshold for leak detection can be established and applied for clinical use. In addition, an algorithm to analyze the data automatically can be developed for its ability to determining uterine integrity.

TABLE 1

Uterine Cavity Integrity Test Results in Test Uteri with Intentionally Created Perforations:

Uterine Cavity Integrity Tests Declared as "NOT SEALED" (n = 12)

| | Flow data as recorded | | No negative flow values | |
| --- | --- | --- | --- | --- |
| | Min $\Delta$ flow | Max flow | Min $\Delta$ flow | Max flow |
| Average | 10.42 | 8.75 | 10.42 | 11 |
| Standard Deviation | 4.38 | 15.55 | 4.3 | 12.64 |
| Maximum | 17 | 38 | 17 | 38 |
| Minimum | 2 | −15 | 2 | 0 |

TABLE 1-continued

Uterine Cavity Integrity Test Results in Test Uteri with Intentionally Created Perforations:

| | Uterine Cavity Integrity Tests Declared as "SEALED" (n = 41[1]) | | | |
|---|---|---|---|---|
| | Flow data as recorded | | No negative flow values | |
| | Min Δ flow | Max flow | Min Δ flow | Max flow |
| Average | 3.12 | 2.34 | 3.12 | 2.41 |
| Standard Deviation | 2.19 | 2.17 | 2.19 | 2.07 |
| Maximum | 8.00 | 6.00 | 8.00 | 6.00 |
| Minimum | 0.00 | −1.00 | 0.00 | 0.00 |

In Table 1, Min Δ flow refers to the minimum change in flow rate over a 15 second window of flow, shown in ml/min. Max flow refers to the maximum flow rate observed in a 15 second window of flow, shown in ml/min. No negative flow values refers to data points where only positive flow rates are calculated. Negative flow values will not occur with a one way in place.

As another consideration, the size and or shape of the uterus will likely change during the integrity test. Thus, in some embodiments, an average flow rate can be used to determine the integrity of the uterus or the positioning of the device. For example, in one embodiment, if the average flow over a predetermined time period, such as 5 seconds, is zero or lower than a threshold flow rate, then the uterus is likely sealed. In another variation, a 15 second time window can be taken in which the trailing average of data points is tabulated for every 15 second time increment. Other time window increments can be utilized as a standard for data collection.

In some embodiments, the return channel comprises a valve 128c, such as a solenoid valve, that can be activated upon the start of the integrity test to close off the egress of the gas/fluid through the return channel. Alternatively, a one way pump can be utilized. When the return flow of gas/fluid through the return channel is stopped with the valve, a change of flow can be detected by the flow meter 126 on the input line. In addition to determining if there is a leak or if the device is positioned properly, the specifics of the changes in flow (e.g., how the flow reacts to closing of the return line with the valve) can provide the following the indications in some cases: a) The size of the uterine cavity; and b) The presence of a leak or lack of integrity in the system. For instance in clinical use with uteri of varying sizes, an integration under the graphical curve of flow rate versus time provides a volume assessment of the size of uterine cavity. The amount of volume can provide the physician information not only on the size of the uterus, but whether the device is improperly embedded in a false passage (smaller volume amount) or in the peritoneal cavity (larger volume amount).

Figure 4:
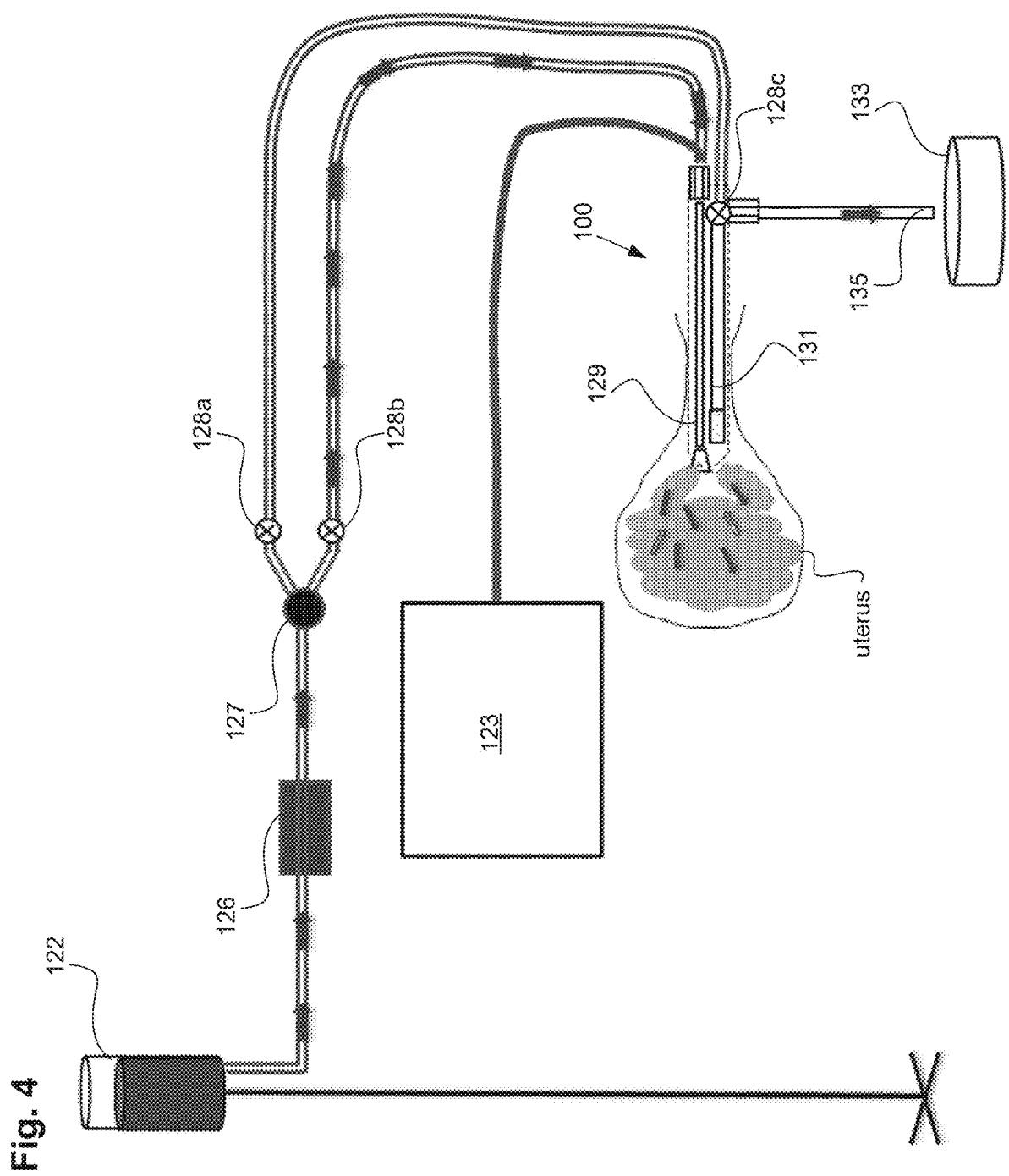
FIG. 4 illustrates one configuration of an apparatus during a uterine patency test.

Referring to FIG. 4, in some embodiments the amount of flow in the inflow and outflow channels can be used to determine the presence of an obstruction that may affect the flow of vapor during the ablation procedure. Based on this determination or patency test, the device may be repositioned or replaced prior to delivery of vapor. For example, in one embodiment, still referring to FIG. 4, a method of performing a patency test can comprise delivering gas or fluid from inflow lumen 129 of the uterine device into the uterus, also referred to as the fluid infusion tip, removing gas or fluid from the uterus with outflow lumen 131 of the uterine device, also referred to as the fluid outflow tip, and determining that the uterine device is not clogged or embedded in tissue if a flow rate of gas or fluid is observed in the flow meter of the inflow lumen of the uterine device. In FIG. 3 and FIG. 4, valves 128a and 128b control the flow of gas/fluid to the uterine ablation device 100 and valve 128c control the flow of gas/fluid from the outflow lumen 131 into the outflow canister or waste container 133. Control of the valves 128a and 128b and 128c can be performed by a separate controller and software unit shown as 123.

If it has been determined that the uterus is sealed based on the integrity test performed and described in FIG. 3, the controller can also be configured to perform a patency test. In one embodiment, referring to FIG. 4, the controller can be configured to open valves 128b and 128c, but close valve 128a. This allows gas or fluid to flow from source 122, through flow meter 126, through one way valve 127 and valve 128b, and into inflow lumen 129. Gas or fluid can be removed through outflow lumen 131, through valve 128c, and into a waste container 133 via tubing 135. As the gas or fluid enters and is removed from the uterus, the flow meter can measure a patency flow rate of the gas or fluid. If the patency flow rate is maintained above a patency flow rate threshold value, the controller can determine that the device is not clogged or embedded into tissue. In some embodiments, observing or measuring a flow of fluid or gas in outflow lumen 131 can be used to determine that the device is not clogged or embedded in tissue.

Figure 7A:
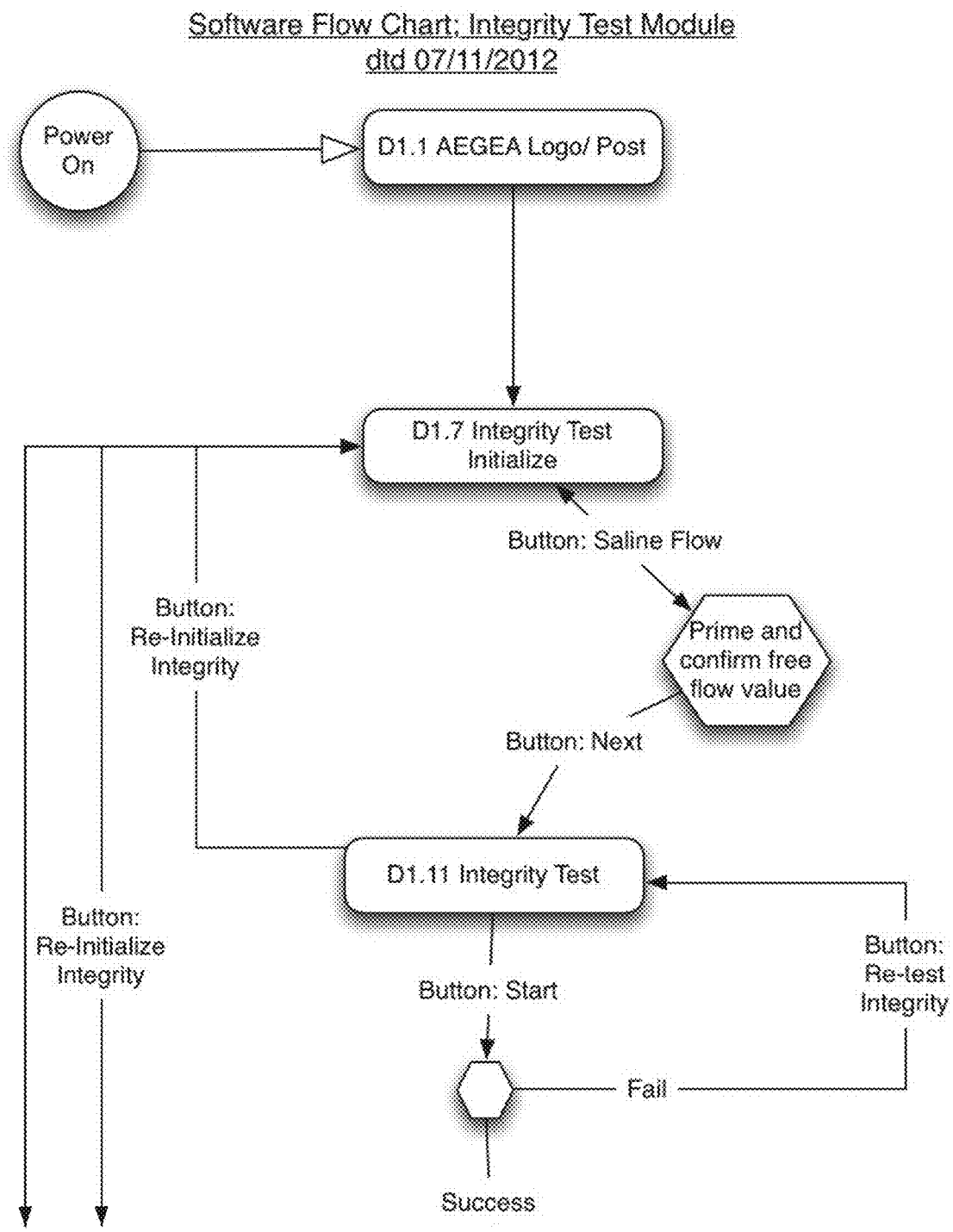
FIGS. 7A-7B illustrate an algorithm for one configuration of a uterine integrity and patency tests.
Figure 7B:
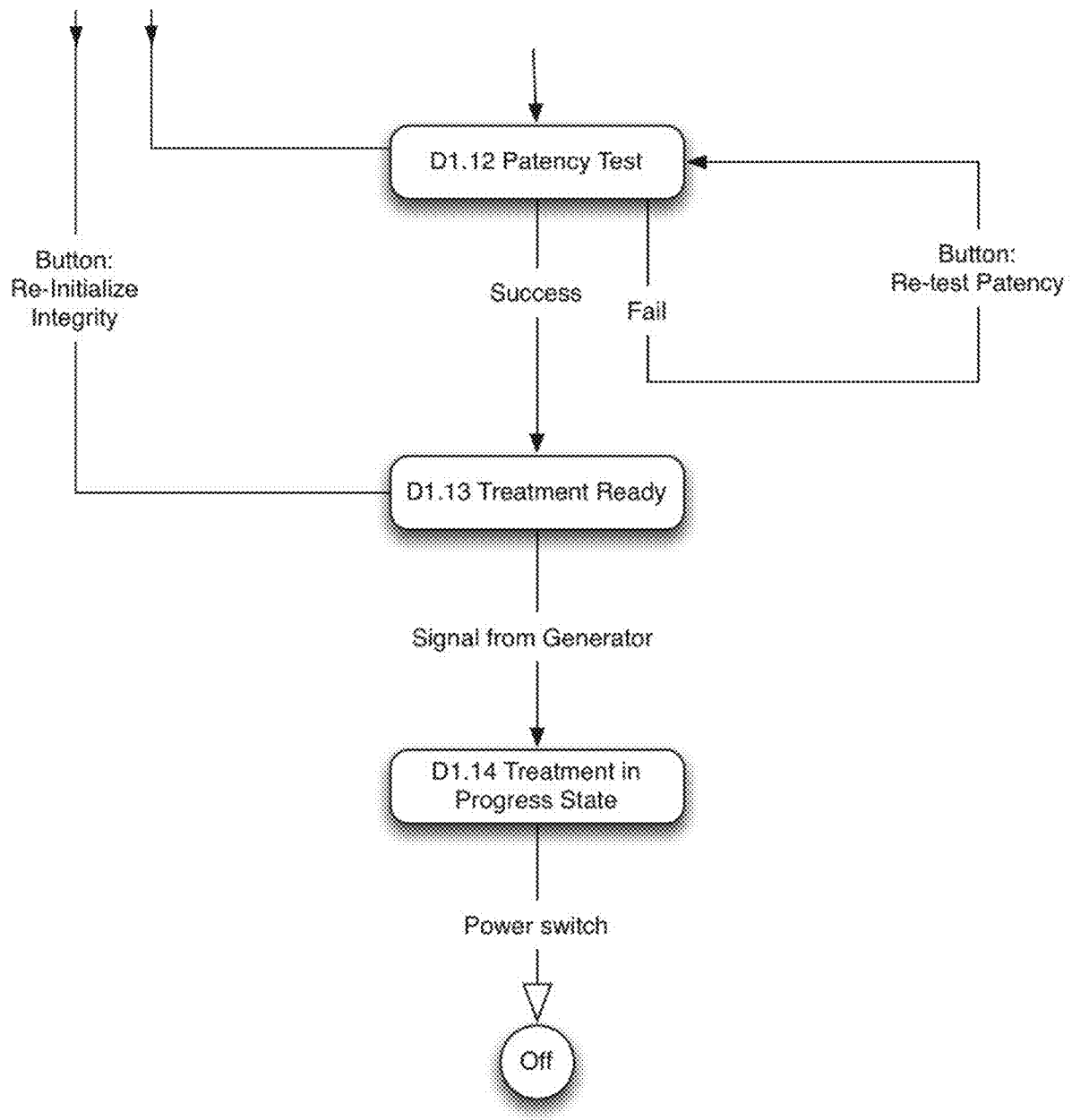

FIG. 7 describes an example of an algorithm for utilizing uterine integrity and patency tests for a uterine ablation procedure. First, a uterine device, as described above, can be inserted into the uterus of a patient. In some embodiments, saline can flow through a flow meter and both the inflow and outflow lumens of the uterine ablation device during insertion into the patient. Once the device has been placed in the uterine cavity, the cervix can be sealed by one or more balloons, such as the distal, central, and proximal balloon described above. Upon sealing the cervix, an integrity test can be initiated. As described above, a flow of gas/fluid from the uterine ablation device can be measured with a flow meter, and the system can monitor for a flow rate through the flow sensor to decrease to a flow rate threshold. Once the flow rate threshold is reached, (e.g., 5 ml/min in one embodiment), it can be determined that the uterus is sealed and the system can then begin the patency test. The patency test maintains flow into the uterine cavity with the inflow lumen of the device, but reverses the outflow lumen to remove gas/fluid from the uterine cavity into a waste container. The flow rate threshold is then monitored during patency test. A flow rate above a patency test threshold (e.g., greater than 5 ml/min in one embodiment) can indicate that the lumens are not clogged or that the distal end of the uterine ablation device is not embedded into tissue. If the patency test threshold is not satisfied, the physician should repeat the insertion steps and repeat the integrity test and patency test prior to initiating uterine ablation. If the patency test threshold is satisfied, the uterine ablation treatment can begin as indicated in FIG. 7.

In some additional embodiments, the return channel for the integrity test may or may not be the same return line used in the therapeutic mode to evacuate vapor and bodily fluids/tissue from the uterus. More specifically, in some embodiments the device may have its own dedicated return channel system specifically for carrying out the integrity test. In another embodiment, the return channel may have its own passive outflow regulator. In yet another embodiment, the return channel could have a second flow meter (not shown) that can be used to compare flow coming into the uterine cavity (via flow meter 126) versus the flow monitored on the egress from the uterine cavity (via the second flow meter within the return channel). Comparing the flow-out versus the flow-in can provide a dynamic measurement for the presence of leaks in the uterus or a lack of integrity.

In an additional embodiment, a system can be employed combining both a solenoid valve and a second flow meter in the return channel. In this embodiment, a series of return channel closures by the solenoid valve in combination with the measurement of flow during open cycles can provide indications of uterine cavity integrity and the amount of volume in that space. In some embodiments a recording and data analysis system can be incorporated to analyze the flow rate measurements and provide automation of actions based on the integrity of the uterus and position of the ablation device. This analysis system records the flow rate at various stages of the treatment and provides appropriate feedback to the user and ablation device.

Figure 5:
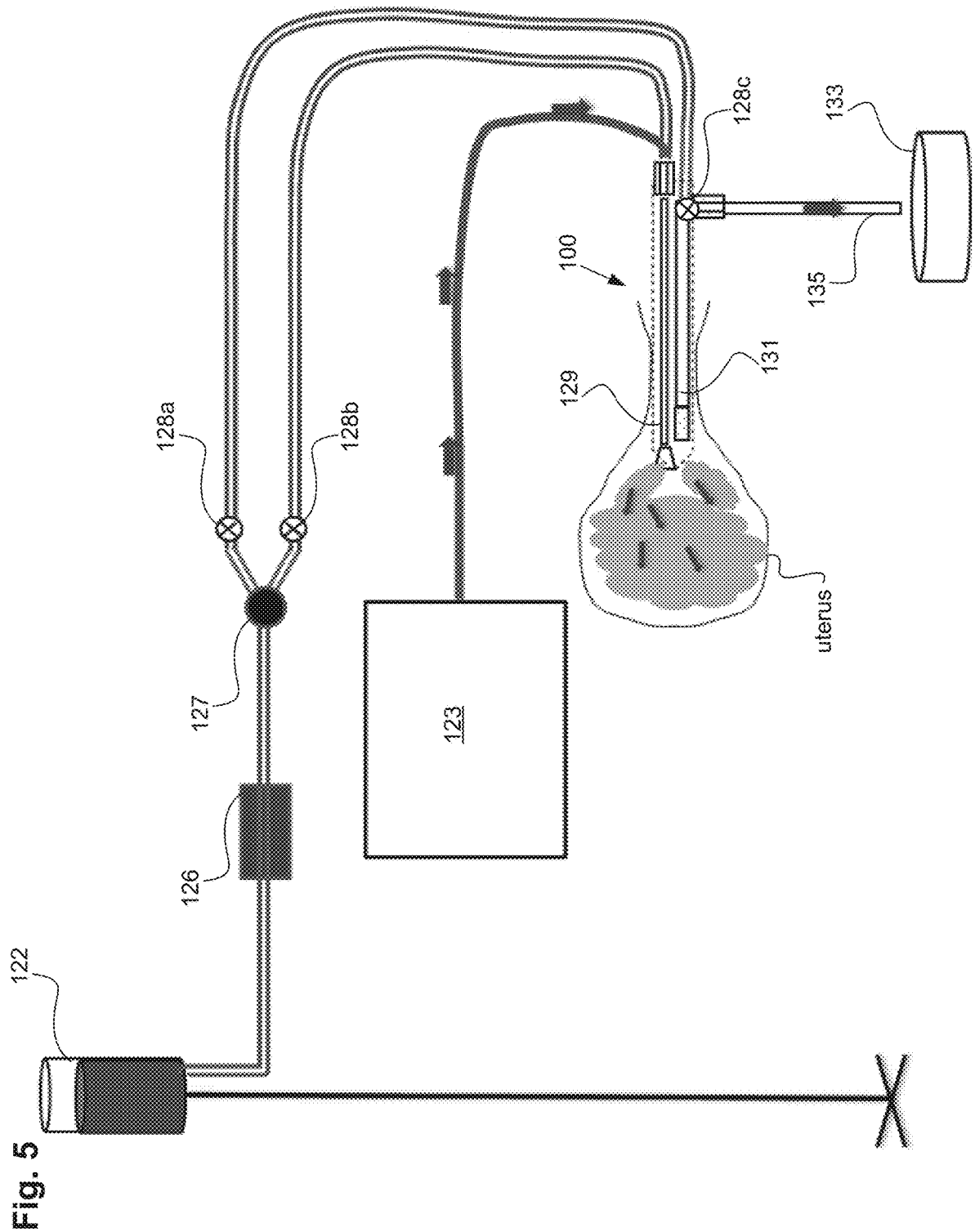
FIG. 5 illustrates one configuration of a uterine ablation device during a vapor treatment operation.

Once the device has been properly positioned and the integrity test and patency tests determine that the uterus is sealed, the device is properly placed and an open communication between the delivery and return lumen exists, a heated condensable vapor can be delivered from the distal tip 106 of ablation device 100 through vapor ports 107 (of FIGS. 1A-1B) to the uterus to ablate the uterine tissue. FIG. 5 illustrates another view of the ablation device delivering vapor to the uterus. In one embodiment, vapor can be delivered to the ablation device via vapor source 123. In another embodiment, not shown, the gas/fluid source 122 can be used to provide a fluid, such as saline, to the device where it can then be converted into vapor to deliver to the uterus. Once the vapor has been delivered to the uterus through inflow lumen 129, the vapor can be removed from the uterus through outflow lumen 131 and deposited in waste container 133 via tubing 135.

Maintaining uterine distension or pressure within the uterine cavity during integrity and patency tests, and immediately prior to the initiation of vapor treatment without deflation May or may not be performed. In some embodiments, a distended uterine cavity under a pressure below 70 mm HG without deflation will experience less blood and debris accumulation within the inflow and outflow lumens of the uterine ablation device prior to treatment. Reducing the accumulation of blood and debris in the return or outflow lumens will reduce procedure time and improve treatment efficiency. Reducing the accumulation of blood and debris in the return or outflow lumen can occur for a time duration encompassing the insertion of the device into the uterine cavity to the initiation of ablation treatment, which in cases can be 1 to 5 minutes. Greater time durations benefit further from the reducing the accumulation of blood and debris.

The initiation of vapor treatment can begin immediately following the completion of the integrity and patency tests. In some embodiments, this action can be controlled by software within the main generator unit. Alternatively, the integrity and patency tests can be conducted by a unit or module separate from the main generator that provides an indication that the treatment procedure is ready to begin utilizing the algorithm illustrated in FIG. 7. The opening and closing of various lumens during the integrity and patency tests can be performed by solenoid valves or balloons that pinch off the lumens.

In one embodiment, utilizing saline over gas as the media for performing the integrity and patency tests has the following advantages. It has been empirically determined that the application of heated vapor may not traverse an intentionally placed perforation in a uterine cavity whereas the same intentionally placed perforation can be traversed by saline media during an integrity test. In addition, in a uterine cavity of a living patient in test conditions, active bleeding can occlude or impede the ability of gas to traverse an intentionally created perforation, thereby providing a false indication of uterine integrity to the physician. For example, the perforating instrument can be a cervical dilator of 3 mm in diameter and the angle of perforation can be 15 degrees to normal, or perpendicular, to the uterine surface. Smaller and larger diameter instruments can be utilized.

Saline is also readily available in clinical use. In practice, gas such as carbon dioxide is administered to a patient within a safety threshold flow rate typically below 100 ml/min and at this rate, the gas may be ineffective in removing blood or other debris in the uterine cavity that may occlude or impede the interpretation of a potential perforation.

Also, in clinical use, incorporating saline over gas as the media for the integrity and patency tests provides a rinsing source for the lumens in vivo. This rinsing or diluting action can facilitate the open communication between the input and output lumens of the uterine ablation device prior to vapor treatment.

Figure 6A:
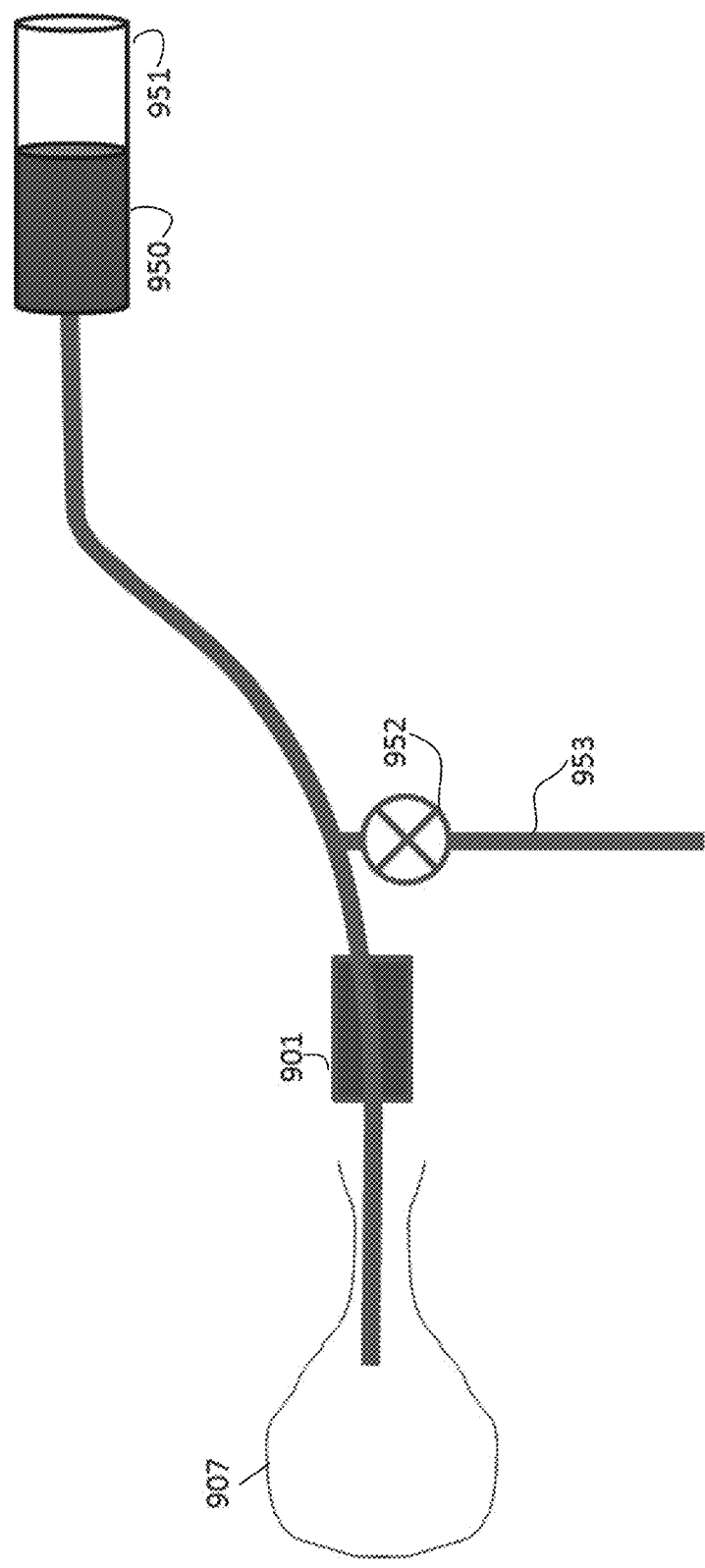
FIG. 6A illustrates one configuration of an apparatus during a uterine integrity test.

Alternatively, an entirely flow-driven system may be used to perform the integrity and patency tests. In the flow driven system, as seen in FIG. 6A, a fluid 950 may be delivered distally towards the device and uterus. The fluid 950 may be saline, for example. The fluid 950 may be housed in a container 951. The container 951 may drive the fluid at a known or a variable rate. For example, in one embodiment the container 951 may be a syringe or peristaltic pump. The fluid 950 may be a gas and the container 951 may contain a propeller to propel the fluid. A valve 952 with a set crack pressure may be positioned proximal to a flow sensor 901. The valve 952 may have a crack pressure set at 60-70 mm Hg, for example. Before the pressure in the uterus reaches the crack pressure of the valve 952, the flow sensor 901 may see a non-zero flow value. Once the pressure inside of the uterus 907 equals the crack pressure of the valve 952, the fluid 950 will cease flowing into the uterus 907 and may instead flow into a lumen 953. The lumen 953 may exit into atmosphere and provide no back pressure. A continued non-zero flow value may indicate a non-sealed uterus. The flow sensor may instead be positioned on line 953 if the flow value at the container 951 is known or measured. Positioning the flow sensor on line 953 may be advantageous to keep the flow sensor 953 out of the sterile field. The flow-driven system described herein may be performed without monitoring or measuring pressure within the uterine cavity.

Figure 6B:
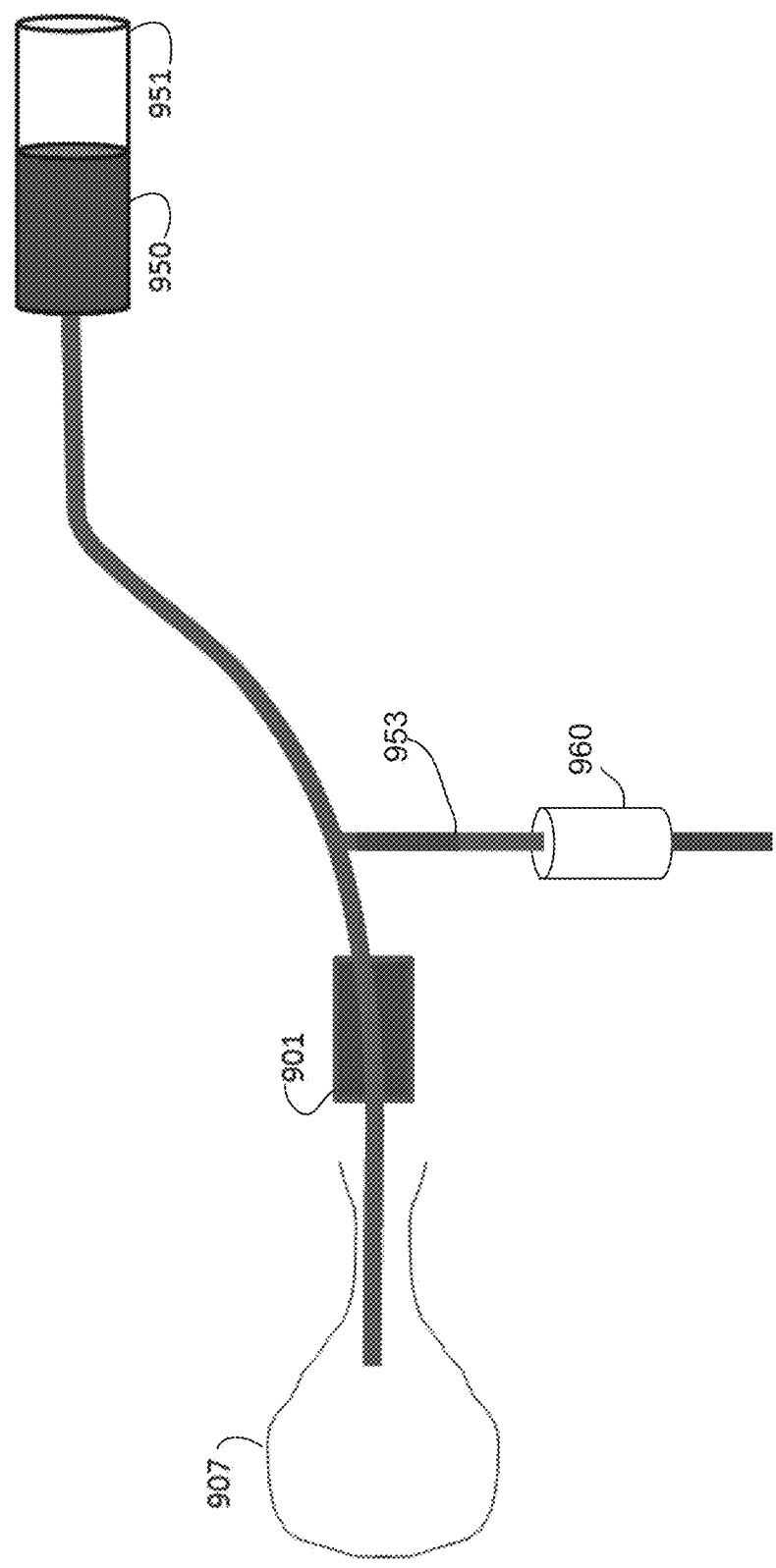
FIG. 6B illustrates another configuration of an apparatus during a uterine integrity test.

As another embodiment, a system for performing an integrity test can be independent of pressure and as an example, remove the requirement for setting the height of a saline source to a know level. In addition, some embodiments can remove the requirement for placing a pressure relief valve within the system with a known cracking pressure. To illustrate this embodiment, as seen in FIG. 6B, a delivery flow of the fluid 950 is known and can be set to a constant value, for example by a pump 951, then an orifice 960 with a known resistance to the fluid may be placed in-between the fluid source and the uterus 907. Orifice 960 can be any component with a known orifice or bore size, such as, for example, a hypodermic needle with a known caliber and inner diameter. The orifice 960 may be positioned at a known height relative to the uterus 907. For example, the orifice 960 may be placed in the handle of the intrauterine device. The orifice 960 may be tuned with the flow of the fluid to yield a predictable pressure in the uterus 907. For example, if the fluid 950 is flowing at 10 mL/min and the orifice has an inner diameter of 0.01 inches and a length of 0.5 inches, then the intrauterine pressure may never exceed a threshold value, such as 60 mm Hg. For example, when the pressure in the uterus is zero (gauge), then the majority of the fluid 950 may flow into the uterus 907. As the uterus 907 is filled with the fluid 950, the pressure in the uterus 907 may increase and the excess fluid 950 may instead flow through the orifice 960. Eventually, all of the fluid 950 may flow through the orifice 960. A flow sensor 901 may be placed as shown in FIG. 6B or may be placed on lumen 953 so as to measure flow through the orifice, for example. The lumen 953 and/or the flow sensor 901 may be completely and/or partially outside of the sterile field. An integrity test may be performed by monitoring the flow of the fluid 950 using the flow sensor 901. For example, if all of the fluid 950 is being diverted through the orifice 960, then the uterus may be considered fully sealed.

In some embodiments for vapor treatment, the shaft of the uterine ablation device can include a thermocouple or other temperature sensor positioned proximally of the positioning balloon or sealing balloon to sense and indicate a vapor leak from the uterus into the cervical canal. In some embodiments the uterine ablation device may incorporate a pressure sensor to indicate a vapor leak in the uterus while the ablation treatment is in progress. During the ablation treatment vapor is delivered through the inflow lumen and exits through the outflow lumen. The amount of vapor delivered into the cavity is controlled by the generator to maintain a predetermined pressure.

In some embodiments, flow meters and valves may be incorporated within the uterine device itself, referred to as the handle, as opposed to being separate components on conduits shown in the drawings.

As for additional details pertinent to the present invention, materials and manufacturing techniques may be employed as within the level of those with skill in the relevant art. The same may hold true with respect to method-based aspects of the invention in terms of additional acts commonly or logically employed. Also, it is contemplated that any optional feature of the inventive variations described may be set forth and claimed independently, or in combination with any one or more of the features described herein. Likewise, reference to a singular item includes the possibility that there are plural of the same items present. More specifically, as used herein and in the appended claims, the singular forms "a," "and," "said," and "the" include plural referents unless the context clearly dictates otherwise. It is further noted that the claims may be drafted to exclude any optional element. As such, this statement is intended to serve as antecedent basis for use of such exclusive terminology as "solely," "only" and the like in connection with the recitation of claim elements, or use of a "negative" limitation. Unless defined otherwise herein, all technical and scientific terms used herein have the same meaning as commonly understood by one of ordinary skill in the art to which this invention belongs. The breadth of the present invention is not to be limited by the subject specification, but rather only by the plain meaning of the claim terms employed.

What is claimed is:

1. A uterine treatment device, comprising:
   a shaft sized and configured for insertion into a uterus of a patient;
   a sealing balloon disposed on the shaft and for sealing the uterus;
   an inflow lumen and an outflow lumen disposed along a length of the shaft;
   at least one inflow port disposed at a distal end of the inflow lumen;
   at least one outflow port disposed at a distal end of the outflow lumen;
   a one way valve disposed in the inflow lumen and configured to reduce or eliminate retrograde flow from the uterus back through the uterine treatment device;
   a gas/fluid source operatively coupled to the inflow lumen and the outflow lumen;
   at least one flow meter disposed between the gas/fluid source and the shaft; and
   a controller configured to perform a uterine integrity test by delivering gas or fluid from the gas/fluid source through the inflow lumen into the uterus without allowing for gas or fluid to be removed from the uterus, detecting with the at least one flow meter an integrity flow rate of gas or fluid as the gas or fluid is delivered into the uterus, and determining that the uterus is sealed if the integrity flow rate decreases below an integrity flow rate threshold value.

2. The uterine treatment device of claim 1, wherein if the controller determined that the uterus is sealed, the controller is further configured to deliver gas or fluid from the gas/fluid source through the at least one inflow lumen into the uterus, remove gas or fluid from the uterus with the outflow lumen, detect with the at least one flow meter a patency flow rate of gas or fluid, and determine whether the uterine treatment device is clogged or embedded in tissue based on the patency flow rate.

3. The uterine treatment device of claim 1, wherein the one way valve is configured to prevent retrograde flow and sinusoidal wave forms in response to uterine contractions.

4. The uterine treatment device of claim 1, wherein the at least one flow meter is disposed in the outflow lumen.

5. The uterine treatment device of claim 1, wherein the controller is configured to determine that the uterus is sealed if the integrity flow rate decreases below the integrity flow rate threshold value within a predetermined time period.

6. The uterine treatment device of claim 1, wherein the controller is configured to determine that the uterus is sealed if the integrity flow rate decreases to zero after a predetermined time period.

7. The uterine treatment device of claim 1, wherein the controller is configured to determine that the uterine treatment device is clogged or embedded in tissue if the patency flow rate is zero.

8. The uterine treatment device of claim 1, wherein the controller is configured to deliver a heated condensable vapor through the inflow lumen into the uterus if the controller determines that the uterus is sealed and the uterine treatment device is not clogged or embedded in tissue.

9. The uterine treatment device of claim 1, wherein the controller is configured to assess a volume of gas or fluid delivered or assess the integrity flow rate to estimate a location of a distal tip of the uterine treatment device within the uterus.

10. The uterine treatment device of claim 9, wherein assessing the volume indicates that the distal tip is in a false passage.

11. The uterine treatment device of claim 9, wherein assessing the integrity flow rate indicates that the distal tip is in a false passage.

12. The uterine treatment device of claim 1, the controller being further configured to perform a patency test by allowing gas or fluid to flow from the gas/fluid source into the uterus, removing the gas or fluid from the uterus, and monitoring the patency flow rate of gas or fluid measured by the at least one flow meter.

13. The uterine treatment device of claim 12 further comprising:
   a first valve disposed between the gas/fluid source and the inflow lumen;
   a second valve disposed between the gas/fluid source and the outflow lumen;
   wherein the controller is configured to perform the uterine integrity test by opening the first valve and closing the second valve, wherein the controller is configured to perform the patency test by opening the first and second valves.

14. The uterine treatment device of claim 12 further comprising:
   a first valve disposed between the gas/fluid source and the inflow lumen;
   a second valve and a third valve disposed between the gas/fluid source and the outflow lumen;
   wherein the controller is configured to perform the uterine integrity test by opening the first valve and the second valve and closing the third valve to allow gas or fluid to flow into the uterus through both the inflow and outflow lumens, wherein the controller is configured to perform the patency test by opening the first valve and the third valve and closing the second valve to allow gas or fluid to flow into the uterus through the inflow lumen and to remove gas or fluid from the uterus through the outflow lumen.

* * * * *